US009538947B2

(12) United States Patent
Mori et al.

(10) Patent No.: US 9,538,947 B2
(45) Date of Patent: Jan. 10, 2017

(54) METHOD, SYSTEM AND DEVICE FOR ASSISTING DIAGNOSIS OF AUTISM

(75) Inventors: Norio Mori, Shizuoka (JP); Katsuaki Suzuki, Shizuoka (JP); Kenji Tsuchiya, Shizuoka (JP); Chie Shimmura, Shizuoka (JP); Hirohisa Sakurai, Shizuoka (JP); Keijyu Tokutani, Shizuoka (JP)

(73) Assignee: National University Corporation Hamamatsu University School of Medicine, Hamamatsu-shi, Shizuoka (JP)

( * ) Notice: Subject to any disclaimer, the term of this patent is extended or adjusted under 35 U.S.C. 154(b) by 194 days.

(21) Appl. No.: 14/342,760

(22) PCT Filed: Sep. 4, 2012

(86) PCT No.: PCT/JP2012/072440
§ 371 (c)(1),
(2), (4) Date: Apr. 4, 2014

(87) PCT Pub. No.: WO2013/035684
PCT Pub. Date: Mar. 14, 2013

(65) Prior Publication Data
US 2014/0213930 A1    Jul. 31, 2014

(30) Foreign Application Priority Data

Sep. 5, 2011    (JP) ................. 2011-192387

(51) Int. Cl.
*A61B 5/16*    (2006.01)
*G06K 9/00*    (2006.01)
*A61B 3/113*    (2006.01)

(52) U.S. Cl.
CPC ............... *A61B 5/16* (2013.01); *G06K 9/0061* (2013.01); *A61B 3/113* (2013.01); *A61B 5/168* (2013.01)

(58) Field of Classification Search
CPC ............. A61B 3/13; A61B 5/16; A61B 5/168; G06K 9/0061
(Continued)

(56) References Cited

U.S. PATENT DOCUMENTS 6,260,968 B1    7/2001    Stark et al.
6,820,979 B1 *  11/2004   Stark ..................... A61B 3/112
                                                351/206
(Continued)

FOREIGN PATENT DOCUMENTS

JP    3453911 B2       10/2003
JP    2004-283609 A    10/2004
(Continued)

OTHER PUBLICATIONS

Thibault et al, Maturation of the sensitivity for luminance and contrast modulated patterns during development of normal and pathological human children, 2007, Vision Research 47, pp. 1561-1569.*
(Continued)

*Primary Examiner* — Adam J Eiseman
(74) *Attorney, Agent, or Firm* — Westerman, Hattori, Daniels & Adrian, LLP

(57) ABSTRACT

Method, system and device for assisting diagnosis of autism which enable assistance of early detection and early definite diagnosis of autism (especially in infants) based on objective evaluation, using a conventionally suggested "eye-gaze detection technique". The method for assisting diagnosis of autism of a subject uses an eye-gaze detecting unit, the unit having at least an imaging camera portion. The method includes displaying, at the position in front of the subject along the direction of the eye gaze of the subject, an illusionary image contained in a plane of an illusion-causing image on a displaying device. The eye-gaze position infor-
(Continued)

mation of the subject looking at the plane is detected, and the eye-gaze position information of the subject is input into an eye-gaze position information storage portion The eye-gaze positions of the subject can be evaluated using a algorithm for assisting diagnosis of autism.

6 Claims, 16 Drawing Sheets

(58) Field of Classification Search
USPC .......................................................... 600/558
See application file for complete search history.

(56) References Cited

U.S. PATENT DOCUMENTS

| 2004/0196433 | A1 | 10/2004 | Durnell | |
|---|---|---|---|---|
| 2006/0238707 | A1 | 10/2006 | Elvesjo et al. | |
| 2011/0242486 | A1* | 10/2011 | Ebisawa | G06F 3/013 351/206 |

FOREIGN PATENT DOCUMENTS

| JP | 2006-507054 | A | 3/2006 |
|---|---|---|---|
| JP | 4181037 | B2 | 11/2008 |
| JP | 4452835 | B2 | 4/2010 |
| JP | 4452836 | B2 | 4/2010 |
| JP | 4491604 | B2 | 6/2010 |
| JP | 4517049 | B2 | 8/2010 |
| JP | 4528980 | B2 | 8/2010 |
| WO | 2010/063064 | A1 | 6/2010 |
| WO | 2010/105370 | A1 | 9/2010 |

OTHER PUBLICATIONS

Bertone et al, Motion Perception in Autism: A "Complex" Issue, 2003, Journal of Cognitive Neuroscience 15:2, pp. 218-225.*
International Search Report dated Oct. 23, 2012 issued in corresponding application No. PCT/JP2012/072440.
Francesca Happé, "Autism: cognitive deficit or cognitive style?" Trends in Cognitive Sciences, Jun. 1999, pp. 216-222, vol. 3, No. 6; Extended European Search Report.
Senju, et al., "Atypical eye contact in autism: Models, mechanisms and development", Neuroscience and Biobehavioral Reviews, Jun. 8, 2009, pp. 1204-1214, vol. 33; Extended European Search Report.
Francesca G.E. Happé, "Studying Weak Central Coherence at Low Levels: Children with Autism do not Succumb to Visual Illusions. A Research Note", Journal of Child Psychology and Psychiatry, 1996, pp. 873-877, vol. 37, No. 7; Extended European Search Report.
Extended European Search report dated May 20, 2015, issued in counterpart European patent application No. 12829614.2 (7 pages).

* cited by examiner

Typically developing individual

Individual with autism

Pixels are divided so that the horizontal side is divided into eight and the vertical side is divided into six

| Number | Position coordinate | Acquisition time | Presence (area) | S→N | S←N |
|---|---|---|---|---|---|
| 000000 | X=----, Y=---- | 00:00000 | -- | None | None |
| 000001 | X=0103, Y=0202 | 00:01666 | S | None | None |
| 000002 | X=0111, Y=0193 | 00:03333 | S | None | None |
| 000003 | X=0120, Y=0188 | 00:04999 | S | None | None |
| 000004 | X=0134, Y=0180 | 00:06666 | S | None | None |
| ... | | | | | |
| 001200 | X=0189, Y=0110 | 40:00000 | N | None | SHIFT |

METHOD, SYSTEM AND DEVICE FOR ASSISTING DIAGNOSIS OF AUTISM

TECHNICAL FIELD

The present invention relates to a method, system and device for assisting diagnosis of autism. More particularly, the present invention relates to a method, system and device for assisting diagnosis of autism using an eye-gaze detection technique, each assisting early definite diagnosis of patients of autism. Hereinafter, the term "autism" is used as a generic term including autism related diseases, such as Asperger syndrome and Asperger disorder (pervasive development disorder with abnormality in sociality, interest and communication), and the present invention can be applied also to these autism related diseases.

BACKGROUND ART

Autism is one of development disorders with impairment in sociality (prevalence is supposedly 1%). If incorrect diagnosis or detection of autism of a child may result in serious trouble in daily life and school life of the child and, in the child, lowering of self-esteem and development of psychiatric symptoms (such as anxiety and dysphoria) are predicted.

However, established effective medication of autism with has not yet been found. Therefore, the only way to achieve improve prognosis of autism is early diagnosis and early (from the age younger than 3 years old) educational intervention based on the diagnosis.

Currently, it is not easy to surely make early diagnosis of autism with standard clinical technique. In conventional diagnosis of autism, evaluation and diagnosis are conducted by a pediatrician or child psychiatrist based on behavior of infants. However, the number of the experts (specialists) is small and early diagnosis is difficult. Further, objective evaluation is currently difficult since the evaluation result varies depending on evaluators.

In current diagnosis of autism by specialists, experiential determination is made in interview based on appearance, or components of collected blood are examined. However, there is a problem in that the appearance-based determination requires a great deal of experience of specialists and is difficult to quantify. The blood test is accompanied with complication of blood collection. Further, in the examination of infants, these examination means are currently not effective and sure. This is because it is almost impossible to communicate with an infant in an interview and application of the determination based on blood components to an infant of younger than 3 years old is still in the laboratory stage. Further, there is a serious problem of failure or delay in medical consultation because parents of an infant do not detect whether or not the infant is an individual with autism.

In view of current situation above, with respect to autism of not only adults but also children (especially infants), a method, device and assistance system which enable early detection and early definite diagnosis by experts (specialists) based on objective evaluation are desired.

In recent years, it is becoming clear that abnormality is found in the distribution of points of regard of undiagnosed infants with autism. That is, it is becoming clear that an infant with autism is characteristic in that he/she cannot correctly draw attention to an eye gaze of another person. This abnormality is regarded as derived from the essence of autism, impairment in sociality. Further, this abnormality is regarded as a symptom appearing in an extremely early stage.

By the use of a preferable eye-gaze detection technique, this abnormality can be correctly detected and utilized as an objective index for early diagnosis of autism. Based on this idea, the present inventors focused on this abnormality.

In the obtainment of such abnormality in the distribution of points of regard, as a conventional eye-gaze detection technique, for example, a method for detecting eye gaze of a subject, using:

a first imaging camera for measuring the position of a pupil relative to a coordinate system;

a second imaging camera having a light source arranged at a known position in the coordinate system and forming a corneal reflection center to obtain data of a distance r from the corneal reflection center to a pupil center and an angle $\phi$ of distance r relative to a coordinate axis of the coordinate system; and a calculation means for calculating the direction of eye gaze based on information from each of the cameras.

Further, some techniques using this method (device, technique and the like for detecting eye gaze) are also suggested (for example, see PATENT LITERATURES 1 to 5).

PATENT LITERATURE 6 discloses, as another technique similar to the "eye-gaze detection technique" of above-mentioned patented invention, an eye detection installation comprising:

one or more light sources for emitting light in directions toward the head of a user, a detector for receiving light from the head of a user and to repeatedly capture pictures thereof, and an evaluation unit connected to the detector for determining the position and/or gaze direction of an eye, wherein the evaluation unit is arranged to determine, in a picture captured by the detector, an area in which an image of an eye or images of eyes is/are located and, after determining the area, to control the detector to forward to the evaluation unit information about successive or following pictures that only corresponds to the determined area of the image captured by the detector.

PATENT LITERATURE 7 discloses a device for recognizing eye gaze in which:

an eye is irradiated with light, an image is formed by an imaging camera, the image having 3 or more characteristic points on the cornea of the eye, the center of curvature of the cornea of the eye is determined from the characteristic points of the cornea on the formed image, and the eye-gaze direction is recognized from the information of the center of curvature of the cornea and position of the center of the pupil, the device comprising:

a provisional eye-gaze direction calculating means which calculates a provisional eye-gaze direction from the positional relationship between the center of curvature of the cornea and the center of the pupil, a corneal area determining means which determines a restricted corneal area from the provisional eye-gaze direction and the information of the position of the pupil, a treating means which, when the characteristic points on the image are present within the restricted corneal area, regards the provisional eye-gaze direction as the result of the recognition of eye gaze and, when a portion of the characteristic points on the image is not present within the restricted corneal area, selects additional characteristic points on the image present within the restricted corneal area, determines additional center of curvature of the cornea of the eye from the additional characteristic points on the image selected, recognizes additional eye-gaze direction from the information of the additional center of curvature of the cornea and position of the center of the pupil, and regards the additional eye-gaze direction as the result of the recognition of eye gaze.

PATENT LITERATURE 8 discloses an eye tracking system for monitoring the movement of a user's eye, the system comprising:

(a) video data input means for receiving video data produced by eye imaging means (imaging camera) monitoring the user's eye;
(b) spot location means for determining, from the video data, the location of a reference spot formed on the user's eye by illumination of the user's eye by a point source of light, the spot location means including adaptive threshold means for providing an indication of parts of the image produced by the eye imaging means which have a brightness greater than a threshold value, and spot identification means for selecting a valid reference spot by comparing the parts of the image with predetermined validity criteria;
(c) pupil location means for determining, from the video data, the location of the centre of the pupil of the user's eye relative to the reference spot in order to determine the user's line of gaze,
the pupil location means comprising:
a selection means which selects a pupil tracking window comprising a portion of the image produced by the eye imaging means, the portion corresponding to the location of the valid reference spot;
an edge selecting means which selects the edge of the pupil by selection of those parts of the gradient of the image portion in the pupil tracking window which have a gradient greater than a threshold value; and
a centre determining means which determines the centre of the pupil by referring to the points selected for the edge of the pupil;
the centre determining means comprising:
a triad selection means for substantially randomly selecting three superthreshold pixels to form a triad for further processing, from among a plurality of pixels of pupil image data; and
a triad processing means for determining the centre and radius of a hypothetical circle passing through each of the selected pixels; and
(d) display means for indicating the user's point of regard from the user's line of gaze determined by the pupil and spot location means.

However, any prior art in which the above-mentioned "eye-gaze detection technique" and the like using at least an Imaging Camera Portion is applied to assistance of diagnosis of autism has not yet been found.

Incidentally, as described later, in the present invention, an infant is characterized as an individual to which such an "eye-gaze detection technique" can be applied. Especially, each of the techniques of the above-mentioned PATENT LITERATURES 1 to 5 is one of the techniques suitable for an infant who has small pupils, cannot understand what is spoken and might not stand still as instructed.

CITATION LIST

Patent Literature

PATENT LITERATURE 1: Japanese Patent No. 4517049
PATENT LITERATURE 2: Japanese Patent No. 4452835
PATENT LITERATURE 3: Japanese Patent No. 4452836
PATENT LITERATURE 4: Japanese Patent No. 4491604
PATENT LITERATURE 5: Japanese Patent No. 4528980
PATENT LITERATURE 6: Japanese Patent Application prior-to-examination Publication (Kohyo) No. 2006-507054
PATENT LITERATURE 7: Japanese Patent No. 3453911
PATENT LITERATURE 8: Japanese Patent No. 4181037

SUMMARY OF INVENTION

Technical Problem

It is an object of the present invention to provide, in view of the above-mentioned problems, a method, system and device for assisting diagnosis of autism which enable assistance of early detection and early definite diagnosis of autism (especially in infants) based on objective evaluation, using a conventionally suggested "eye-gaze detection technique".

Solution to Problem

The present inventors have made extensive and intensive studies with a view toward developing to solve the above-mentioned problems. As a result, it has unexpectedly been found that the difference in tendency of eye-gaze movement between typically developing (healthy) children (hereinbelow referred to as "typically developing individuals" including adults, children and infants) and children with autism (hereinbelow referred to as "individuals with autism" including adults, children and infants) as subjects can be detected using the above-mentioned "eye-gaze detection technique" by applying the "eye-gaze detection technique", such as those mentioned in the above-mentioned prior art documents, to the above-mentioned abnormality in the distribution of points of regard of infants with autism (which is regarded as derived from the essence of autism, impairment in sociality, and also regarded as a symptom appearing in an extremely early stage) as a technique for correctly detecting this abnormality and, in conjunction with this technique, displaying a specific "illusionary image" with a specific construction to the subjects. The present invention has been completed, based on this novel finding.

The above-mentioned detection of difference in tendency of eye-gaze movement corresponds to detection of the symptom derived from the essence of autism, impairment in sociality, from the eye-gaze movement to suggest an objective index for early diagnosis of autism, not to medical practice (definite diagnosis). The present invention enables assistance of diagnosis with improved convenience. For example, an examination itself only for data detection can be conducted, even in an area with a small number of experts (specialists) or in a case with no expert (specialist) present (such as a group examination in a school or local health center). The definite diagnosis can be made by an expert (specialist), later or immediately for early detection, based on the evaluation result of the detected data, even in a distant place using a communicating means. Further, recommendation by a doctor of another medical field or the like to obtain definite diagnosis by an expert (specialist) based on the evaluation result of the detected data becomes available.

That is, according to the first aspect of the present invention, there is provided a method for assisting diagnosis of autism of a subject using an eye-gaze detecting unit, the unit having at least an Imaging Camera Portion, the method comprising:

displaying, at the position in front of the subject along the direction of the eye gaze of the subject, an illusionary image contained in a plane of an illusion-causing image on a displaying device, detecting eye-gaze position information of the subject looking at the plane, inputting the eye-gaze position information of the subject into an eye-gaze position information storage portion, and evaluating the eye-gaze positions of the subject using a predetermined algorithm for assisting diagnosis of autism.

According to the second aspect of the present invention, there is provided the method according to the first aspect, wherein the following images (a) and (b):
(a) a particular illusionary image which is an image causing optic illusion that the image is seemingly moving when the eyes are pulled slightly away, and
(b) a non-illusionary image causing no optic illusion are arranged in parallel in the plane, in order to avoid intended leading of moving of the eye gaze of the subject or let the subject voluntarily look at images displayed.

According to the third aspect of the present invention, there is provided the method according to the second aspect, wherein the non-illusionary image (b) is an image which is similar to the particular illusionary image (a) in appearance and color but causes no optic illusion that the image is seemingly moving even when the eyes are pulled slightly away.

According to the fourth aspect of the present invention, there is provided the method according to any one of the first to third aspects, wherein the predetermined algorithm is constructed based on the contrast or difference in tendency of eye-gaze movement between typically developing individuals and individuals with autism that the frequencies of eye-gaze movements of typically developing individuals looking at an illusionary image are high but those of individuals with autism looking at an illusionary image are low.

According to the fifth aspect of the present invention, there is provided the method according to the fourth aspect, wherein the contrast or difference in tendency of eye-gaze movement between typically developing individuals and individuals with autism is found from the frequencies detected from the eye-gaze position information, wherein the eye-gaze positions given in the eye-gaze position information are found in the following areas (i) and (ii) of the plane:
(i) an area in which the illusionary image is displayed
(ii) an area other than the area (i), and wherein each of the frequencies is detected based on one of the following (a) to (c):
(a) the accumulated total time or average time for each of the areas (i) and (ii) in which the eye-gaze positions are present in each area,
(b) the number of movements of the eye-gaze positions from the area (i) to the area (ii), or
(c) the longest time for each of the areas (i) and (ii) in which the eye-gaze position is continuously present in each area.

According to the sixth aspect of the present invention, there is provided the method according to the first aspect, wherein the predetermined algorithm sets a threshold value for the frequency of mutual eye-gaze movement between an area of the plane in which the illusionary image is displayed and an area of the plane in which the illusionary image is not displayed, based on a database having stored therein previously obtained information of eye-gaze positions of subjects and definite diagnosis of each of the subjects as to whether or not the subject is an individual with autism.

According to the seventh aspect of the present invention, there is provided a system for assisting diagnosis of autism, which comprises:
(a) an eye-gaze detecting means which detects eye-gaze position information of a subject looking at a plane of an illusion-causing image displayed at the position in front of the subject along the direction of the eye gaze of the subject using an eve-gaze detecting unit having at least an Imaging Camera Portion,
(b) a means for inputting the eye-gaze position information of the subject,
(c) an eye-gaze evaluating means which evaluates the eye-gaze position information of the subject using a predetermined algorithm for assisting diagnosis of autism, based on the eve-gaze position information obtained when an illusionary image is displayed, the illusionary image being an image causing optic illusion that the image is seemingly moving when the eyes are pulled slightly away, and
(d) a displaying means which displays the results of evaluation of the eye-gaze positions of the subject.

According to the eighth aspect of the present invention, there is provided the system according to the seventh aspect, which further comprises:
(e) a recording means which records the results of evaluation of the eye-gaze positions of the subject.

According to the ninth aspect of the present invention, there is provided a device for assisting diagnosis of autism using an illusionary image, which comprises:
(i) an eye-gaze detecting portion which detects eye-gaze position information of a subject looking at a plane of an illusion-causing image displayed at the position in front of the subject along the direction of the eye gaze of the subject using an eve-gaze detecting means,
(ii) an eye-gaze information recording portion which records the eye-gaze position information detected by the eye-gaze detecting portion (i),
(iii) an eye-gaze information displaying portion which displays the eye-gaze position information of the subject recorded by the eye-gaze information recording portion (ii),
(iv) an eye-gaze information evaluating portion which conducts evaluation of the eye-gaze position information of the subject displayed by the eye-gaze information displaying portion (iii) using a predetermined algorithm for assisting diagnosis of autism with respect to analogy to eye-gaze information of typically developing individuals or individuals with autism,
(v) an evaluation result outputting portion which outputs the evaluation results obtained by the eye-gaze information evaluating portion (iv), and
(vi) an evaluation result recording portion which records the evaluation results output by the evaluation result outputting portion (v) or obtained by the eye-gaze information evaluating portion (iv).

Effect of the Invention

The method and system of the present invention for assisting diagnosis of autism enables, by applying the "eye-gaze detection technique" disclosed in the above-mentioned PATENT LITERATURE and the like and, in conjunction with this technique, displaying a specific "illusionary image" with a specific construction to subjects, in addition to assistance of early definite diagnosis of patients of autism, indication of high or low possibility of autism and suggestion of necessity of examination even by a non-specialist. Further, the method, system and device of the present invention for assisting diagnosis of autism exhibit an effect that assistance of early detection and early definite diagnosis of autism (even in an infant before the age that the identification by a specialist as an individual with autism can be applied to) based on objective evaluation becomes possible.

DESCRIPTION OF EMBODIMENTS

Figure 1:
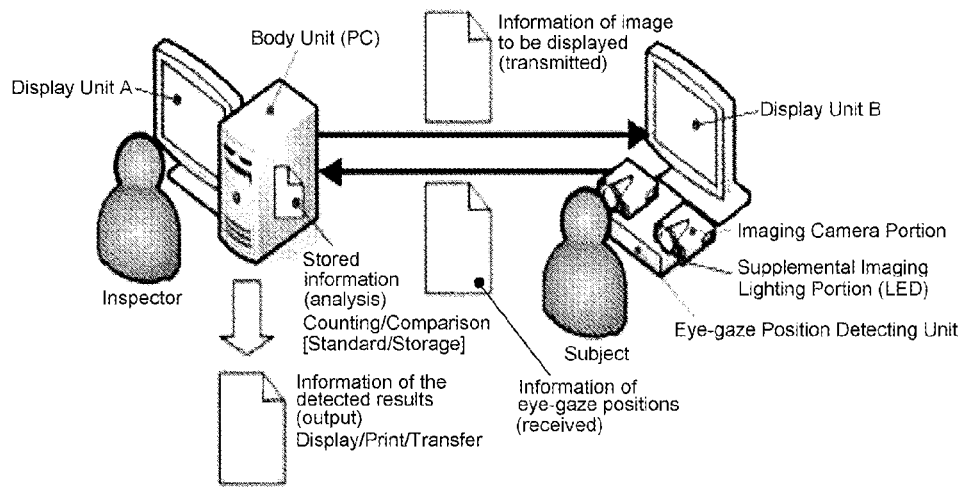
FIG. 1 is a figure schematically showing the construction of the method and system of the present invention for assisting diagnosis of autism.
Figure 2:
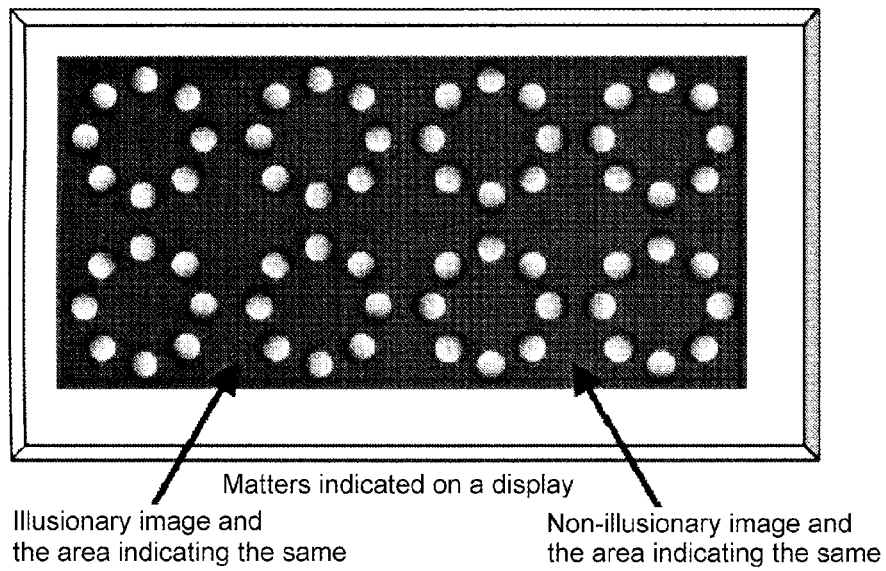
FIG. 2 is a figure showing one example of the plane of an illusion-causing image with the left half indicating an illusionary image causing optic illusion and the right half indicating an image causing no optic illusion.

Hereinbelow, the method, system and the like of the present invention for assisting diagnosis of autism are described in detail.

The method of the present invention for assisting diagnosis of autism comprises:
detecting eye-gaze position information of a subject looking at a plane of an illusion-causing image using an eye-gaze detecting unit,
inputting the eye-gaze position information of the subject into an eye-gaze position information storage portion, and
evaluating the eye-gaze positions of the subject using a predetermined algorithm for assisting diagnosis of autism.

The system of the present invention for assisting diagnosis of autism comprises:
(a) an eve-gaze detecting means which detects eye-gaze position information of a subject looking at a plane of an illusion-causing image displayed at the position in front of the subject along the direction of the eve gaze of the subject using an eye-gaze detecting unit having at least an Imaging Camera Portion,
(b) a means for inputting the eye-gaze position information of the subject,
(c) an eye-gaze evaluating means which evaluates the eye-gaze position information of the subject using a predetermined algorithm for assisting diagnosis of autism, based on the eye-gaze position information obtained when an illusionary image is displayed, the illusionary image being an image causing optic illusion that the image is seemingly moving when the eyes are pulled slightly away, and
(d) a displaying means which displays the results of evaluation of the eye-gaze positions of the subject.

1. Method and system for assisting diagnosis of autism

The method, system and the like of the present invention for assisting diagnosis of autism are described in detail (in the following explanation, for convenience, in an explanation of the above-mentioned system for assisting diagnosis of autism, the method and/or device for assisting diagnosis of autism may be explained).

The construction of devices for the system of the present invention (hereinbelow referred to as the "assistance devices") for assisting diagnosis of autism is explained below.

General explanation of the system construction is made first. The assistance devices for diagnosis are constructed from, for example, Body Unit/Eye-gaze Position Detecting Unit/Display Unit A/Display Unit B and Eye-gaze Position Detecting Unit is constructed from Imaging Camera Portion and, optionally, Supplemental Imaging Lighting Portion.

The above-mentioned Body Unit/Display Unit A are provided in the area of the inspector's side and the above-mentioned Eye-gaze Position Detecting Unit/Display Unit B are provided in the area of the subject's side.

Each of these units is not obstructed to be provided in another unit. This is because in some cases, Body Unit or Eye-gaze Position Detecting Unit may be built into Display Unit A or B, respectively (like single-unit personal computers which are found in commercially available personal computers in recent years) or Eye-gaze Position Detecting Unit may be built into a personal computer provided separately from that as Body Unit. For example, in an extremely integrated construction, the system may have a single-unit construction in which Body Unit and Display Units A and B are integrated (i.e., the units for a subject are also used as those for an inspector), which is operated with mode switching between a subject mode and an inspector mode, i.e., operated under conditions wherein examination of a subject and evaluation by an inspector are not simultaneously conducted.

Each of the units for the area of the subject's side and those for the area of the inspector's side is not limited to be placed in the same room. The present invention includes (i) examination of a subject in a distant place and (ii) evaluation of an image recorded for examination of a subject in which the place of the evaluation is different from the place of the recording and the evaluation is conducted on a date after the date of the recording.

One specific example of the system applicable the present invention to has the construction of FIG. 1.

In FIG. 1, the area allocated to a doctor or his/her substitute for the diagnosis of autism is referred to as the "area of the inspector's side". One example of the construction of units in the area of the inspector's side is as follows. The examination itself for data detection can be conducted not only by a doctor but also his/her substitute.

(1) Body Unit (Commercially Available Personal Computer):

A desktop PC manufactured by Hewlett-Packard Co. (model name: Pavilion Elite HPE)

(3A) Display Unit A (commercially available liquid crystal display):

A display manufactured by iiyama (model name: ProLite E2407HDS, specifications: liquid crystal display, 24 inch)

The area allocated to a subject for the diagnosis of autism is referred to as the "area of the subject's side". One example of the construction of units in the area of the subject's side is as follows.

(2) Eye-Gaze Position Detecting Unit:

A device for detection of points of regard produced by Shizuoka University [the device published in Collection of Papers for Information Science and technology Forum 9(3), 589-591, 2010-08-20, "a device for detection of points of regard with easy calibration by a stereo camera, which allows head movement"]

(2A) Imaging Camera Portion (implemented into the above-mentioned unit (2) as a CCD camera of NTSC type)

(2B) Supplemental Imaging Lighting Portion (implemented into the above-mentioned unit (2) as an LED emission circuit)

(3B) Display Unit B (commercially available liquid crystal display):

A display manufactured by NEC(model name: LCD192VBK, specifications: liquid crystal display, 19 inch)

Next, each unit is explained.

(1) Body Unit

Any commercially available personal computer may be used as Body Unit.

As shown in FIG. 1, Body Unit is appropriately constructed so that specific information of image to be displayed is transmitted to Display Unit B, information of eye-gaze positions of the subject is received from Eye-gaze Position Detecting Unit, and eye-gaze movement of the subject is registered as stored information in which the information of position and time is in conformity with the transmitted information of image to be displayed.

Body Unit further conducts (i) counting, in real time or after the completion of detection, for the determination as to whether the detected eye-gaze movement is specific to an individual with autism or a movement of a typically developing individual, based on the above-mentioned stored information, (ii) optionally after counting (i), comparison of the detected eye-gaze movement with standard eye-gaze movement of an individual identified as a typically developing individual (or individual with autism), and (iii) output of the results of analysis to Display Unit A (including an external output) as information of the detected results.

In addition, by Body Unit, various information of the stored information and/or information of the detected results is not only indicated in Display Unit A but also optionally printed by, indicated in and/or transferred into an external device, as output of information of the detected results.

(2) Eye-Gaze Position Detecting Unit

Eye-gaze Position Detecting Unit (hereinbelow also referred to as "Eye-gaze detecting unit"), which is positioned in the proximity of Display Unit B looked at by the subject, obtains information related to the positions of eye gaze of the subject (hereinbelow also referred to as "information of eye-gaze positions") from Imaging Camera Portion (optionally using also Supplemental Imaging Lighting Portion) and successively outputs information of eye-gaze positions to Body Unit. As a result, Body Unit obtains information of eye-gaze positions as to what portion of Display Unit B the subject looks at.

Any conventional and/or commercially available detection means/device can be applied as Eye-gaze Position Detecting Unit as long as the means/device can detect information of eye-gaze positions of the subject.

Eye-gaze Position Detecting Unit may detect information of eye-gaze positions from only one eye or both of two eyes, depending of the type of the selected device.

In the application of conventional and/or commercially available detection means/device, maximized accuracy of detection of eye-gaze positions of the subject is important.

In connection with this high-accuracy detection, for example, application of the techniques mentioned in the above-mentioned PATENT LITERATURES 1 to 5 (including other techniques of any inventions and applications published) brings construction which enables easy detection of eye gaze with less error, high accuracy and small size of device, even though the detection is accompanied with correction related to (i) an infant as a subject moving around ceaselessly, (ii) a subject wearing glasses, (iii) curvatures of eyes varying depending on subjects and the like. Therefore, in the detection of information of eye-gaze positions, each of these techniques is extremely preferred as a technique for accurately and easily detecting eye gaze.

Although Eye-gaze Position Detecting Unit detects information of eye-gaze positions of the subject in reply to the behavior of and/or in accordance with the instructions from Body Unit and/or Display Unit B, it is not necessary that Eye-gaze Position Detecting Unit operates simultaneously with Body Unit and/or Display Unit B.

If not operates simultaneously, information of eye-gaze positions constantly output from Eye-gaze Position Detecting Unit may be received and subjected to calculation and analysis by Body Unit and/or Display Unit B so that the position of each image in information of image to be displayed and the eye-gaze positions of the subject (while the image is displayed) are specified.

(3) Display Units A and B

Any commercially available display may be used as each of Display Units A and B. There is no particular limitation with respect to the type of each of these units and a liquid crystal display, CRT display, projector or the like can be employed as each of these units. There is no particular limitation with respect to the size and shape of the displaying portion of each of these units.

It is important to pay attention to avoid adverse effect to the analysis and output of Body Unit caused by the difference in size and shape of the displaying screen of each of these units, time lag in the time for displaying, difference relative to past/standard stored information or the like. Appropriate adjustment may be conducted to avoid adverse effect caused by the difference in size, time lag in the time for displaying or the like. For example, information of Display Unit (such as display rate, size and the like) may be added to the stored information and necessary correction is conducted during the comparison.

As each Display Unit, a stereoscopic display (which is commercially available in recent years and may project a sense of depth) may be applied. In connection with application of three-dimensionally detectable eye-gaze position information (although this is an extreme case), Display Unit B includes, in addition to the above-mentioned stereoscopic display, presentation of an object with a stereoscopic shape (such as a diorama) if the cost and labor for preparing this object can be ignored. On the other hand, with respect to two-dimensionally detectable eye-gaze position information, images may be displayed in the manner of slide presentation or picture-story show, in place of presentation in a display, as long as the idea of the present invention can be realized.

(4) Types of Information

In the present invention, information handled by each unit is principally classified into the following 4 types.
 (a) Information of image to be displayed
 (b) Information of eye-gaze positions
 (c) Stored information
 (d) Information of the detected results
Each type of information is explained below.

(a) Information of Image to be Displayed (a-1) Image Contained in the Information of Image to be Displayed In the present invention, "information of image to be displayed" (also referred to as "plane of an image" if the image is a planer image) refers to information of image to be developed at the position in front of the subject along the direction of the eye gaze of the subject. The "information of image" is usually information of a still image or moving image of a diagram, character, illustration, person, landscape and the like. Among these images, an image causing optic illusion is referred to as an "illusionary image".

Among illusionary images in general sense (also referred to as "illusionary figures" or the like) (various examples of illusionary images in this sense is given in the item "optic illusion" in "Wikipedia, The Free Encyclopedia", including those given at http://en.wikipedia.org/wiki/Peripheral drift illusion), some images are those of figures each containing an element causing, when the figure is looked at, optic illusion that a portion of the figure around the point which is looked at is seemingly show vertical, horizontal or rotational wavering, although the image is a still image. Typical examples of such images are Fraser-Wilcox illusion (A. Fraser and K. J. Wilcox: Perception of illusory movement, Nature, 281, 565-566, 1979), Basic figures of optimized Fraser-Wilcox illusion Type IV ("Trick eyes graphics NEO" edited by Akiyoshi Kitaoka, printed by Kanzen, published in August of 2010) and the like, each referred to as "Anomalous motion illusion", "Rotating illusion" or the like. In the present invention, attention is paid to such an illusionary image which is hereinbelow referred to as a "particular illusionary image".

In the present invention, such an illusionary image is applied to information of image to be displayed.

Illusionary images in general sense includes those containing no element perceived as causing, when the image is looked at, optic illusion that a portion of the image around the point which is looked at is seemingly moving. Examples of such an image includes an image with Ebbinghaus illusion. In the present invention, such an image is not included in the "illusionary image", and any image not classified into the "illusionary image" or "particular illusionary image" is generally referred to as a "non-illusionary image".

Examples of some particular illusionary images published on the Internet by some persons in or outside Japan are given below.

Example of Literature Published by a Person in Japan
 http://www.adm.fukuoka-u.ac.jp/fu844/home2/Ronso/Jinbun/L40-1/L4001_0001.pdf Examples of Literature Published by a Person Outside Japan
 http://www.jneurosci.org/content/25/23/5651.full.pdf Further, some typical examples of specific particular illusionary images are summarized in Table 1 below.

TABLE 1

Figure 5:
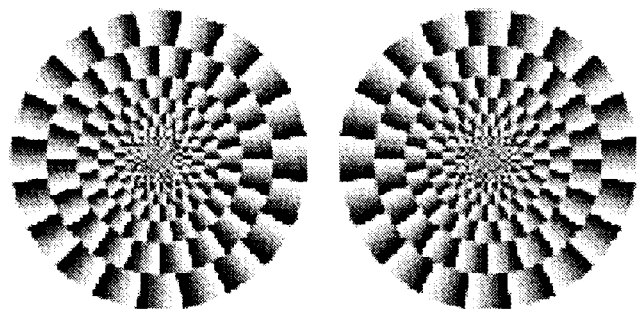
FIG. 5 is a figure showing another example of the plane of an illusion-causing image.
Figure 6:
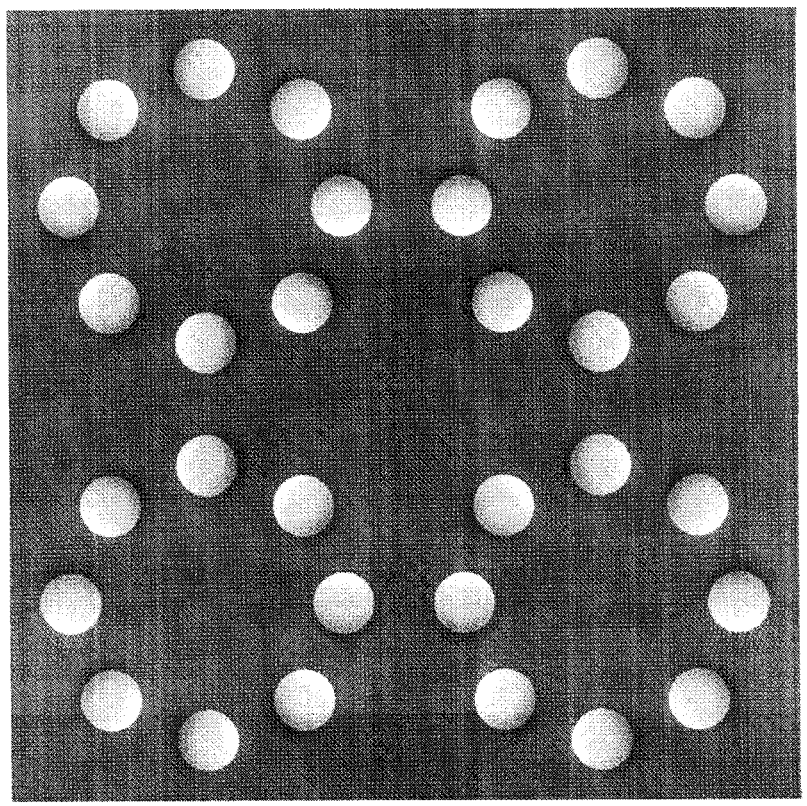
FIG. 6 is a figure showing another example of the plane of an illusion-causing image.
Figure 7:
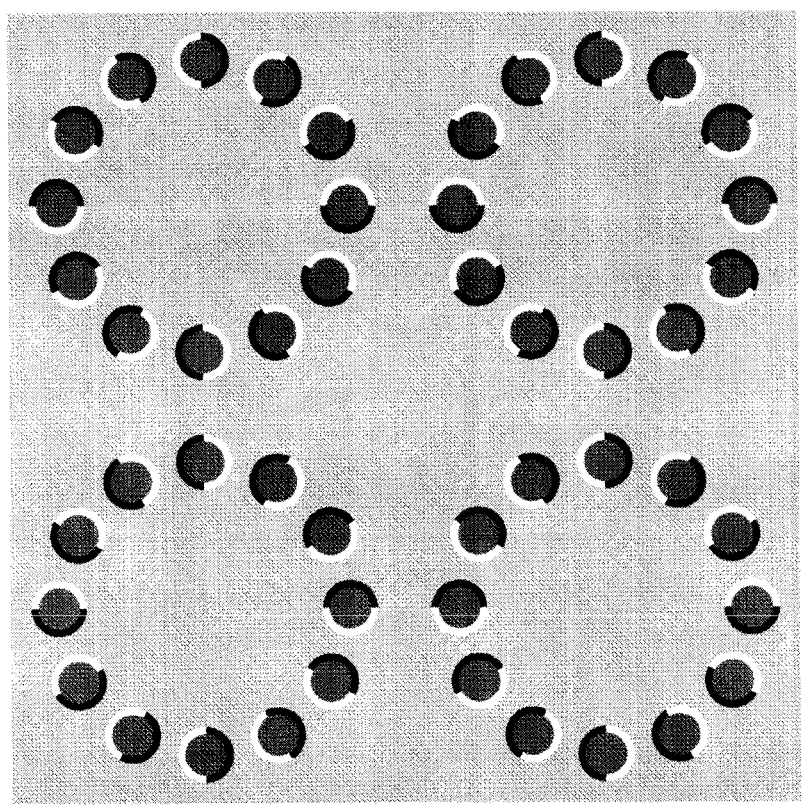
FIG. 7 is a figure showing another example of the plane of an illusion-causing image.
Figure 8:
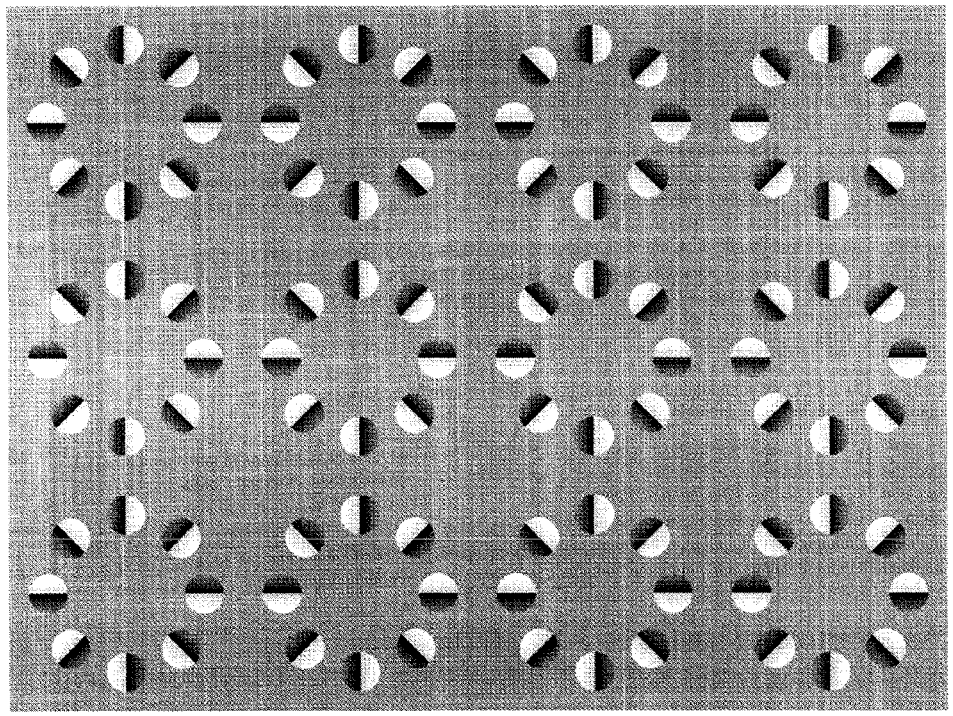
FIG. 8 is a figure showing another example of the plane of an illusion-causing image.
Figure 9:
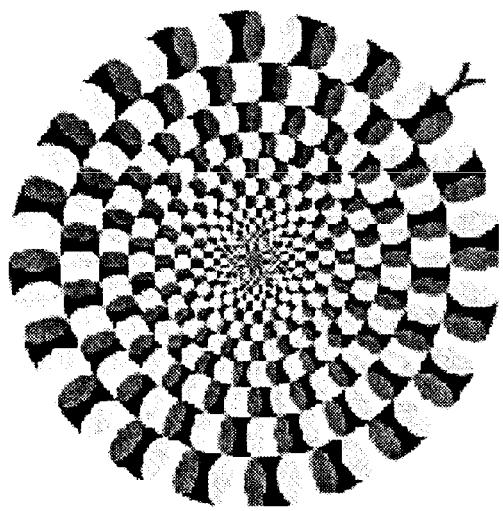
FIG. 9 is a figure showing another example of the plane of an illusion-causing image.
Figure 10:
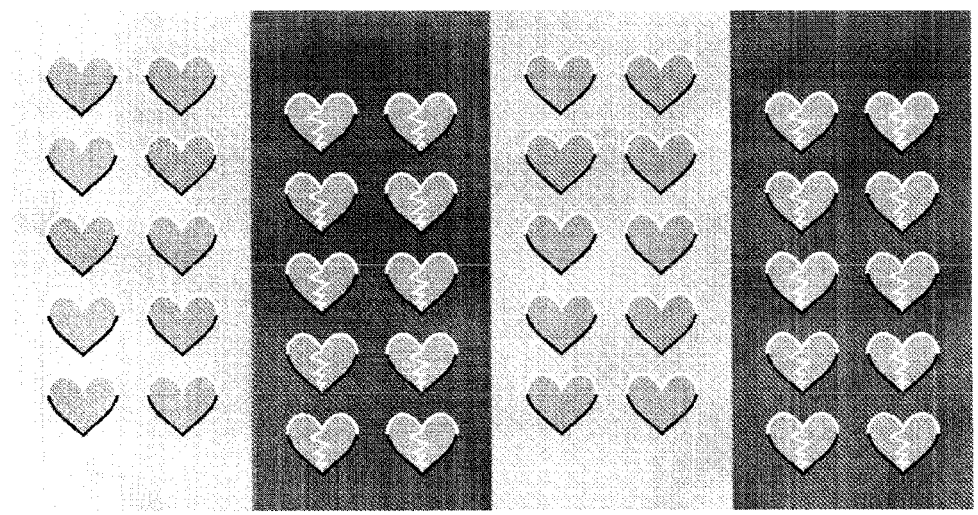
FIG. 10 is a figure showing another example of the plane of an illusion-causing image.
Figure 11:
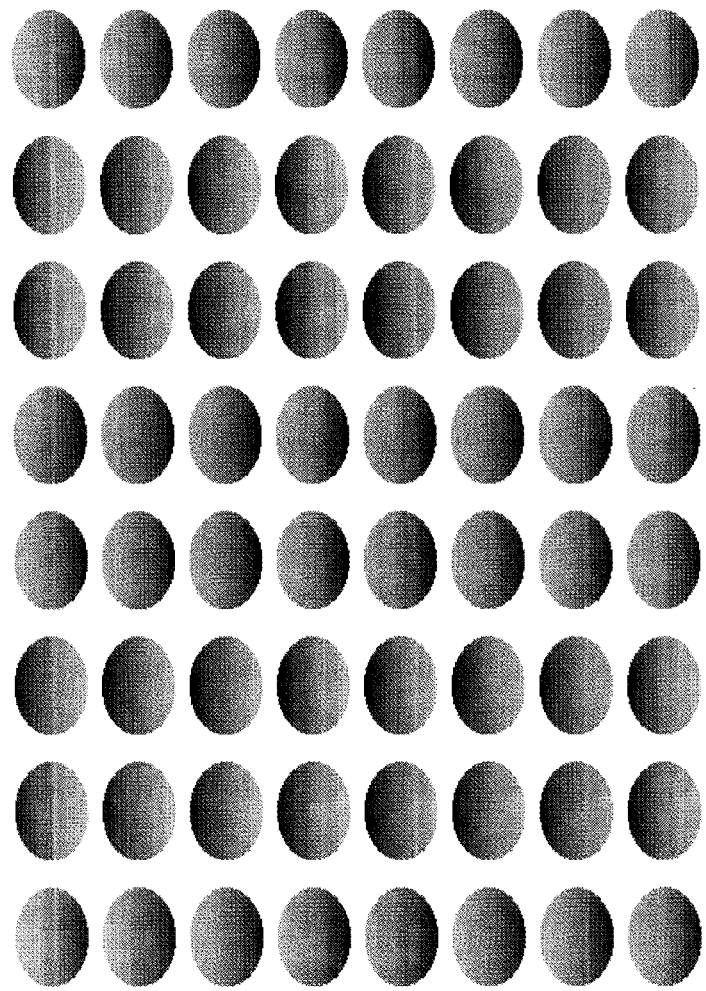
FIG. 11 is a figure showing another example of the plane of an illusion-causing image.
Figure 12:
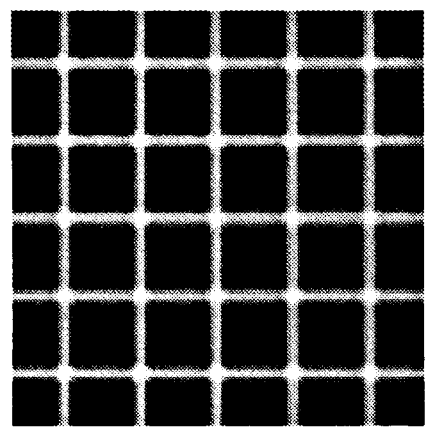
FIG. 12 is a figure showing another example of the plane of an illusion-causing image.
Figure 13:
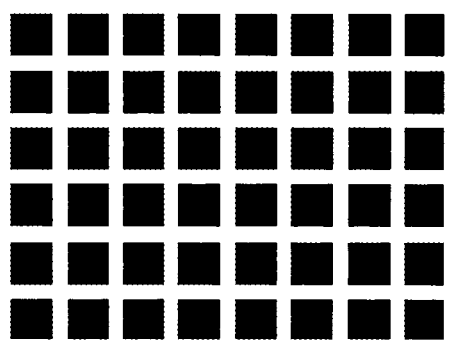
FIG. 13 is a figure showing another example of the plane of an illusion-causing image.

| Name of work | Author (publication or HP) | Corresponding example of the particular illusionary image |
|---|---|---|
| Fraser-Wilcox illusion | Fraser and Wilcox (http://www.psy.ritsumei.ac.jp/~akitaoka/PDrift.pdf) | FIG. 5 |
| Basic figures of optimized Fraser-Wilcox illusion Type IV (provisional) | Akiyoshi Kitaoka (http://www.psy.ritsumei.ac.jp/~akitaoka/rotate16.html) | FIG. 6 |
| Rotating grapes | Akiyoshi Kitaoka (http://www.psy.ritsumei.ac.jp/~akitaoka/rotate16.html) | FIG. 7 |
| Rotating capsule ring | Akiyoshi Kitaoka (http://www.psy.ritsumei.ac.jp/~akitaoka/saishin45.html) | FIG. 8 |
| Rotating snakes | Akiyoshi Kitaoka ("Trick eyes graphics NEO" printed by Kanzen) | FIG. 9 |
| Ascending and descending hearts | Akiyoshi Kitaoka (http://www.psy.ritsumei.ac.jp/~akitaoka/motion21.html) | FIG. 10 |
| Eggs | Akiyoshi Kitaoka (http://www.ritsumei.ac.jp/~akitaoka/motion.html) | FIG. 11 |
| Bergen's illusion | Akiyoshi Kitaoka (http://www.ritsumei.ac.jp/~akitaoka/Bergene.html) | FIG. 12 |
| Hermann grid | Yuuji Baba/Yasuhiro Tanaka ("Tameshite Nattoku Sakushi Zukan" printed by KODANSHA Ltd.) | FIG. 13 |

TABLE 1-continued

Figure 14:
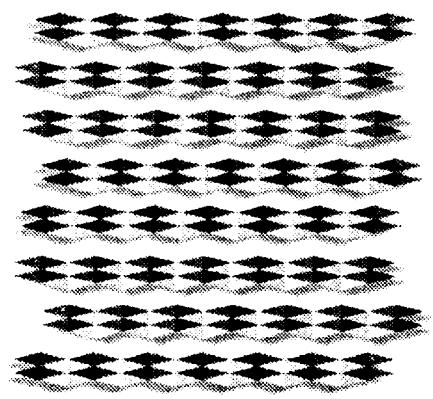
FIG. 14 is a figure showing another example of the plane of an illusion-causing image.
Figure 15:
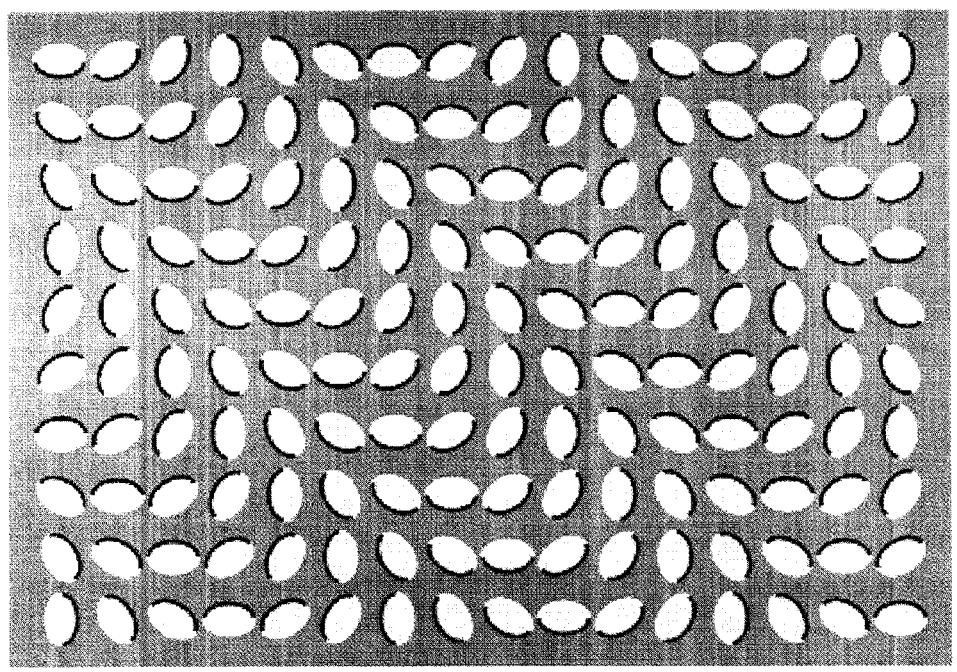
FIG. 15 is a figure showing another example of the plane of an illusion-causing image.
Figure 16:
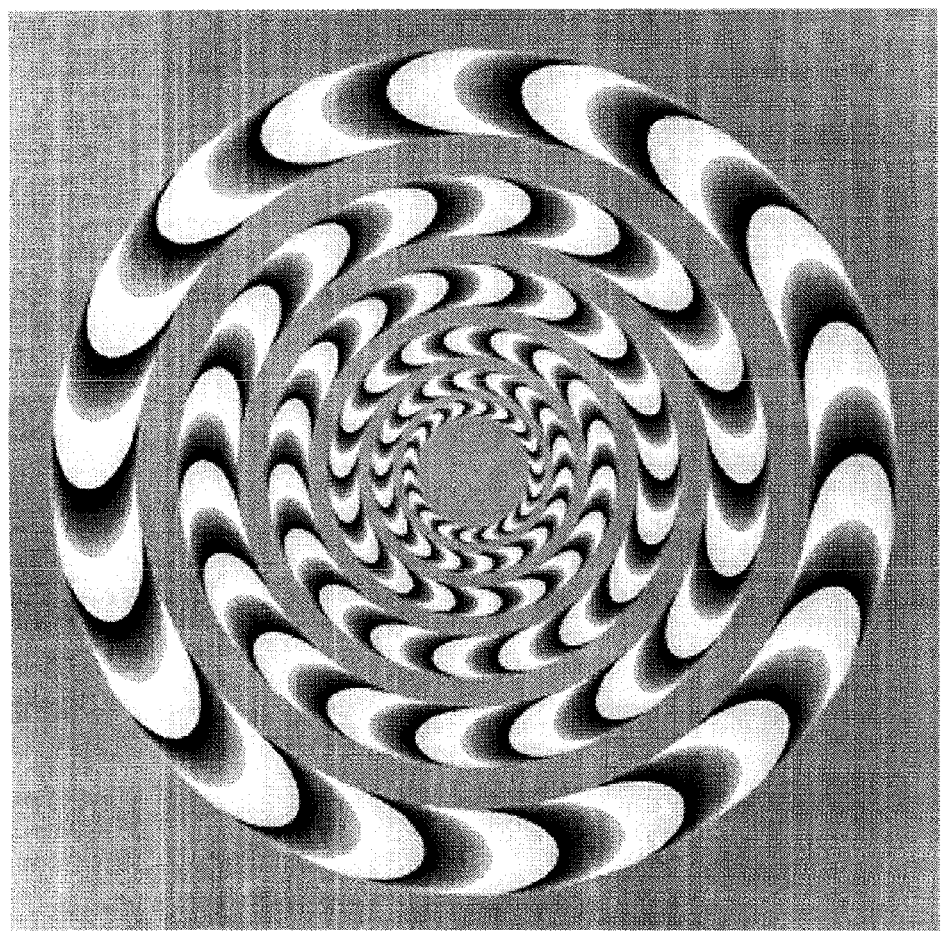
FIG. 16 is a figure showing another example of the plane of an illusion-causing image.

| Name of work | Author (publication or HP) | Corresponding example of the particular illusionary image |
| --- | --- | --- |
| Moving snakes with shadows | Akiyoshi Kitaoka ("Sakushi Nyumon" printed by Asakura Publishing Co., Ltd.) | FIG. 14 |
| Rice wave | Akiyoshi Kitaoka ("Trick eyes graphics NEO" printed by Kanzen) | FIG. 15 |
| Rotating tunnel of red snakes | Akiyoshi Kitaoka ("Trick eyes graphics NEO" printed by Kanzen) | FIG. 16 |

It seems that the mechanism of these particular illusionary images has not yet been completely clarified. However, each of these particular illusionary images is, in common, an image of a figure containing an element causing, when the figure is looked at, optic illusion that a portion of the figure around the point which is looked at (i.e., a portion of the figure within the field of view, except for the center of the field of view (therefore, this portion is not visually in focus)) (in other words, a portion of the figure from which the eyes are pulled slightly away) is seemingly show vertical, horizontal or rotational wavering, although the image is constructed as a still image.

The effect of this illusion is regarded as substantially the same to any individual looking at this kind of image, unless the individual is visually impaired (i.e., the individual is a color-blind individual, individual with imperfect color vision, sightless individual or the like). With respect to a color-blind individual or individual with imperfect color vision, a grayscale image or image with color(s) which can be recognized by the individual may be selected.

Examples of preferred matters to be displayed are given below.

TABLE 2

Figure 17:
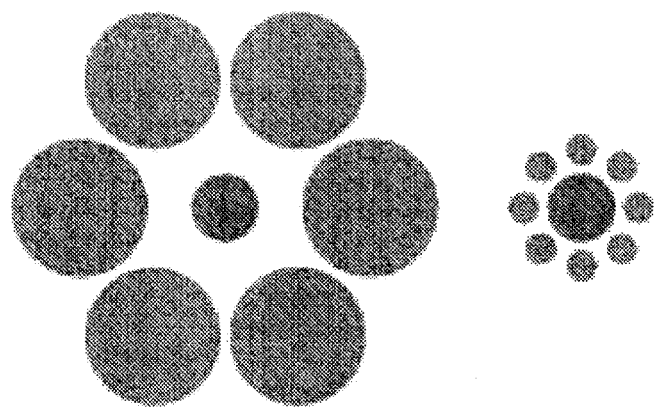
FIG. 17 is a figure showing example (i) in which only an illusionary image is shown across Display Unit B.
Figure 18:
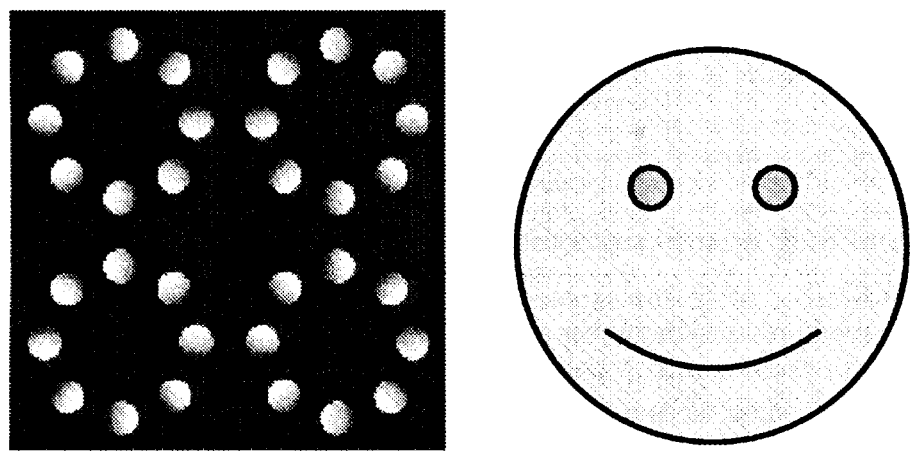
FIG. 18 is a figure showing example (ii) in which an illusionary image and non-illusionary image (α) are placed side-by-side across Display Unit B.
Figure 19:
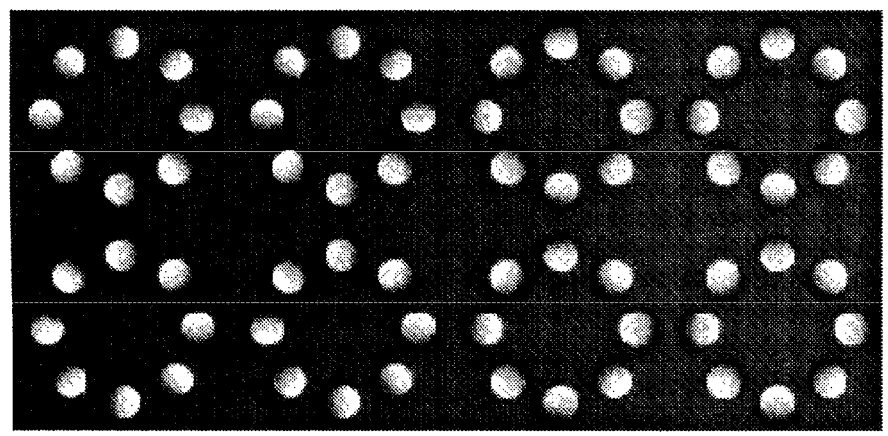
FIG. 19 is a figure showing example (iii) in which an illusionary image and non-illusionary image (β) are placed side-by-side across Display Unit B.

| | (i) Only an illusionary image is shown | (ii) An illusionary image and non-illusionary image (α) are placed side-by-side | (iii) An illusionary image and non-illusionary image (β) are placed side-by-side |
| --- | --- | --- | --- |
| Examples of matters to be displayed on Display Unit B | FIG. 17 | FIG. 18 | FIG. 19 |

In the example of item (i) in Table 2 above, only an illusionary image is shown across Display Unit B with no non-illusionary image. As an example of the illusionary image, an image causing Ebbinghaus illusion is shown across Display Unit B (see FIG. 17).

In the example of item (ii) in Table 2 above, non-illusionary image (α) is an image which is not an illusionary image. This non-illusionary image is shown in the right half of Display Unit B side-by-side in combination with an illusionary image in the left half of Display Unit B so that Display Unit B is wholly covered by this combination. In this example, an image of the face of some character as an example of the non-illusionary image and basic figures of optimized Fraser-Wilcox illusion Type IV as an example of the (particular) illusionary image are placed side-by-side across Display Unit B (see FIG. 18).

In the example of item (iii) in Table 2 above, non-illusionary image (β) is an image which is similar to the particular illusionary image (displayed in a position side-by-side with the position of the non-illusionary image) in appearance (i.e., elements of morphology, such as shape, pattern, color and the like) but causes no optic illusion that, when the image is looked at, a portion of the image from which the eyes are pulled slightly away is seemingly show vertical, horizontal or rotational wavering. In this example, non-illusionary image (β) is shown in the right half of Display Unit B side-by-side in combination with the illusionary image used in the example of item (ii) above in the left half of Display Unit B so that Display Unit B is wholly covered by this combination (see FIG. 19).

An image with no element causing optic illusion, such as non-illusionary image (β) used in the example of item (iii) above, can be prepared from the particular illusionary image. For example, in order to prepare a non-illusionary image from the particular illusionary image used in the above-mentioned examples (constructed from 4 rings in total each constructed from 8 dots), the element causing optic illusion can be deleted by changing the pattern of shading (in other words, color combination of each dot) so that the positions of shadows therein correspond to the shadows produced by a light source from only one direction.

Using such a matter to be displayed (such as that in each of the examples of items (i) to (iii) above in which only an illusionary image is shown across Display Unit B or an illusionary image and non-illusionary image (α) or (β) are placed side-by-side across Display Unit B), eye gaze of a subject can be detected as follows.

A subject looks at some portion of the image displayed on Display Unit B. When an illusionary image is displayed, a subject feels optic illusion. Therefore, the eye gaze of a subject looking at an illusionary image is moved to the position in which the subject feels optic illusion. A subject looking at a particular illusionary image strongly feels optic illusion in a specific potion of the image (i.e., a potion of the image from which the eyes are pulled slightly away), especially when the eye gaze of the subject is moved. Especially, when the eye gaze of the subject is moved to the position in which the subject feels optic illusion, it becomes impossible to feel the optic illusion. Based on this fact, it is possible to lead frequent moving of position on Display Unit B at which the eye gaze of the subject is pointed.

However, when the subject is an individual with autism, the subject does not feel optic illusion or looks at, with a strong will, some portion of the image which the subject himself/herself is interested in. For this reason, a subject with autism naturally tends not to be influenced by the illusion. In other words, in a subject with autism, tendency of frequent moving of position on Display Unit B at which the eye gaze is pointed is poor.

For easy leading of intended moving of the eye gaze of a subject to some specific position, one or both of the displayed illusionary image and non-illusionary image may be horizontally moved, blinked or the like. However, employment of a plane of a still image as information of image to be displayed enables detection of naturally occurring moving of the eye gaze of the subject without intended leading of moving of the eye gaze of the subject. In addition, this is especially preferred for an infant as a subject who is difficult to verbally communicate.

Each of the examples of items (i) to (iii) above is specifically explained below. In the example of item (i) above in which only an illusionary image (or particular illusionary image) is shown across Display Unit B, it is possible to let the subject recognize the position at which optic illusion is felt and lead intended moving of eye gaze to that position.

In the example of item (ii) above in which a particular illusionary image and non-illusionary image (α) are placed side-by-side across Display Unit B (with some character as non-illusionary image (α) in the specific example given in the example of item (ii) in Table 2 above), the device of the present invention first make the subject understand that the matter displayed across Display Unit B has two major components (i.e., composed of two images), the above-mentioned character and particular illusionary image, as well as the positional relationship of these components with the character occupying the right half of the displayed matter and the particular illusionary image occupying the left half of the displayed matter.

In this case, it is possible to make the subject have the following feeling. When the eye gaze position corresponds to that in which the subject looks at the character displayed in the right half of the displayed matter, a portion of the particular illusionary image is positioned in the left side of the field of view of the subject. This portion makes the subject feel optic illusion that the portion is seemingly show vertical, horizontal or rotational wavering, and consciously look at the particular illusionary image. When the eye gaze is subsequently pointed to the particular illusionary image itself, the illusion is deleted and the above-mentioned portion becomes still.

As a result, movement of eve gaze of the subject between the particular illusionary image and non-illusionary image (α) can be led using the positional relationship between these images inducing feeling of optic illusion in the particular illusionary image.

In the example of item (iii) above in which a particular illusionary image and non-illusionary image (β) are placed side-by-side across Display Unit B, the displayed matter seemingly comprises a plurality of the same images jointed to each other to wholly cover Display Unit B (as the specific example given in the example of item (iii) in Table 2 above).

Such a construction of the displayed matter is preferred, because naturally occurring moving of the eye gaze of the subject with a will of the subject himself/herself can be led with no lead to or restriction of the position to be looked at, while avoiding, using the above-mentioned combination of the particular illusionary image and non-illusionary image which are seemingly the same, moving of the eye gaze led by stimulation with difference in pattern or the like.

In this case, the subject looks at each image displayed in Display Unit B with a will of the subject himself/herself. Then, the subject recognizes optic illusion, among the particular illusionary image and non-illusionary image which are seemingly the same, only in a specific portion of the particular illusionary image. When the subject looks at the above-mentioned specific portion in which the optic illusion is recognized, the subject then recognizes that the illusion is deleted and the above-mentioned portion becomes still. Further, the subject further looks at each image displayed with a will of the subject himself/herself and recognizes optic illusion in another specific portion of the particular illusionary image. This is because the subject is interested in the feeling of strangeness/unnaturalness brought by the fact that the displayed matter contains both of portions each (seemingly) shows moving and other portions each shows no moving, although the displayed matter seemingly comprises a plurality of the same images. Using such a behavior of the subject, moving of the eye gaze of the subject between the particular illusionary image and non-illusionary image (β) can be led.

Body Unit makes Display Unit B display such an illusionary image for a period of from several seconds to several tens of seconds. In an image displayed across the displaying device (in other words, the screen of the display or the like), an illusionary image may occupy whole of the image or only some portion of the image (for example, if the image displayed across the displaying device is divided into 2 portions, an illusionary image may occupy only in one of the 2 portions).

The illusionary image to be displayed may comprise only one kind of the illusionary image, a plurality of the same illusionary images or 2 or more different kinds of the illusionary images. Further, the illusionary image may be displayed as a moving image such as an image moving horizontally and/or vertically.

These manners of display are advantageous since a plurality of (particular) illusionary images to be displayed may used and a specific illusionary image suitable for evaluation with respect to each subject can be selected based on the feature of eye gaze movement.

The particular illusionary image is not limited to be displayed only once, and the particular illusionary image may be displayed more than once. Further, interruptive display of an image with no optic illusion may be conducted before or after the display of the particular illusionary image (and between two displays among a plurality of the displays of the particular illusionary image).

Interruptive display of an image with no optic illusion is regarded as advantageous for studying the conditions effective for analysis, since this display may consciously prevent advanced eye gaze movement to a specific portion at which a specific image is displayed or cancel (reset) feeling of habituation of the subject.

(a-2) Setting of Areas of an Image Contained in the Information of Image to be Displayed In typically developing individuals looking at an illusionary image, the significant eye-gaze movements are observed. On the other hand, in individuals with autism looking at an illusionary image, the frequencies of eye-gaze movements tend to be low. In the present invention, diagnosis of autism is conducted based on this contrast or difference in tendency of eye-gaze movement between typically developing individuals and individuals with autism. This diagnosis is realized using an algorithm to set areas in an image (element) contained in the information of image to be displayed.

In the pattern/image as described above, two types of areas in the image, "illusionary area S" and "non-illusionary area N" as explained below are set, depending on the type of the image.

Each of these areas in the image is related to information of positions in the image displayed on Display Unit B. Hereinbelow, this information of positions is referred to as "areal information".

First, the area in the image displayed on Display Unit B in which area an illusionary image is displayed is defined as "illusionary area S".

With respect to an illusionary image displayed on the displaying device, an area (with no image) surrounding the outer edge of the illusionary image is set. Hereinbelow, this area is referred to as a "peripheral area" of the illusionary image. Illusionary area S is set as the whole area within (surrounded by) the peripheral area of the illusionary image. The peripheral area may be arbitrarily set so that the distance between the outer edge of the peripheral area and the outer edge of the illusionary image is increased and the peripheral area is increased.

Figure 20:
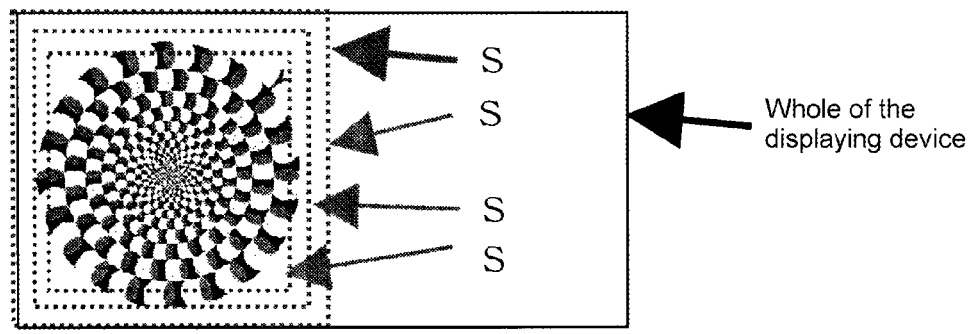
FIG. 20 is a figure showing one example explaining specific illusionary area S.

For example, with respect to an illusionary image with a complicated shape of the outer edge, illusionary area S may be arbitrarily set so as to have an outer edge with a simple shape (such as a rectangle, circle or the like) and completely surround the illusionary image. A plurality of illusionary areas each having a shape with geometrical similarity may be set, the illusionary areas overlapping to each other and the outer edge(s) of some of the illusionary areas intersecting the outer edge of the illusionary image (see FIG. 20). In this case, these illusionary areas are numbered S1, S2, S3 . . . from the illusionary area with the outermost outer edge for convenience and, with respect to one on these illusionary areas having an outer edge completely surrounded by the outer edge of another one on these illusionary areas, the size of the illusionary area may be smaller than the size of the illusionary image with the size of the another illusionary image somewhat larger than the size of the illusionary image.

The above setting is advantageous in the case wherein, for example, with respect to a subject looking at an illusionary image, the subject should be judged as looking at a point around the outer edge of the illusionary image (or looking at the illusionary image, considering the error range of accuracy specific to the eye-gaze detecting unit used), even when the eye-gaze position is detected at the point slightly out of the area of the illusionary image.

Figure 21:
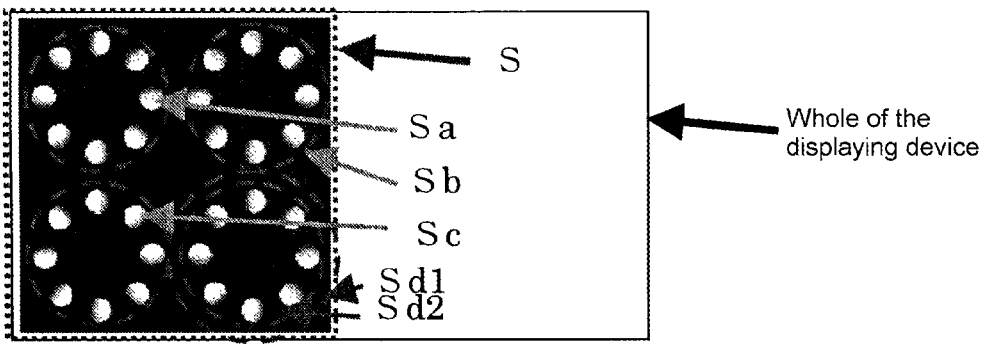
FIG. 21 is a figure showing another example explaining specific illusionary area S.

When 2 or more illusionary images (which may be the same or different) are simultaneously displayed as mentioned above, one illusionary area surrounding all of these illusionary images may be set or, when two illusionary images are positioned with some space between them, two separate illusionary areas each surrounding one of these illusionary images may be set (see FIG. 21). In this case, these illusionary areas are numbered Sa, Sb . . . for convenience. Also in this case, a plurality of illusionary areas overlapping to each other and the outer edge(s) of some of the illusionary areas intersecting the outer edge of each illusionary image may be set. In this case, with respect to each groups of the illusionary areas, these illusionary areas are numbered Sd1, Sd2 . . . from the illusionary area with the outermost outer edge for convenience.

As apparent from the above, although it is possible to set one illusionary area for each illusionary image, it is preferred to divide one illusionary area to a plurality of portions (for example, an area corresponding to one illusionary image is vertically or horizontally divided into two halves). Especially, division of each illusionary area to many small portions is advantageous, since this division may enable, by analysis of the stored information, obtainment of various information, such as information as to (a) which position in the illusionary area, for each illusionary area, the eye gaze of the subject is focused on, (b) to what extent the subject looks at the positions in the peripheral area of the illusionary area (not the illusionary image itself) or outside the illusionary area, and the like. Such information may be useful for some necessary adjustment for another calculation and/or comparison of the stored information, such as adjustment for broadened error range of accuracy specific to the eye-gaze detecting unit.

Figure 22:
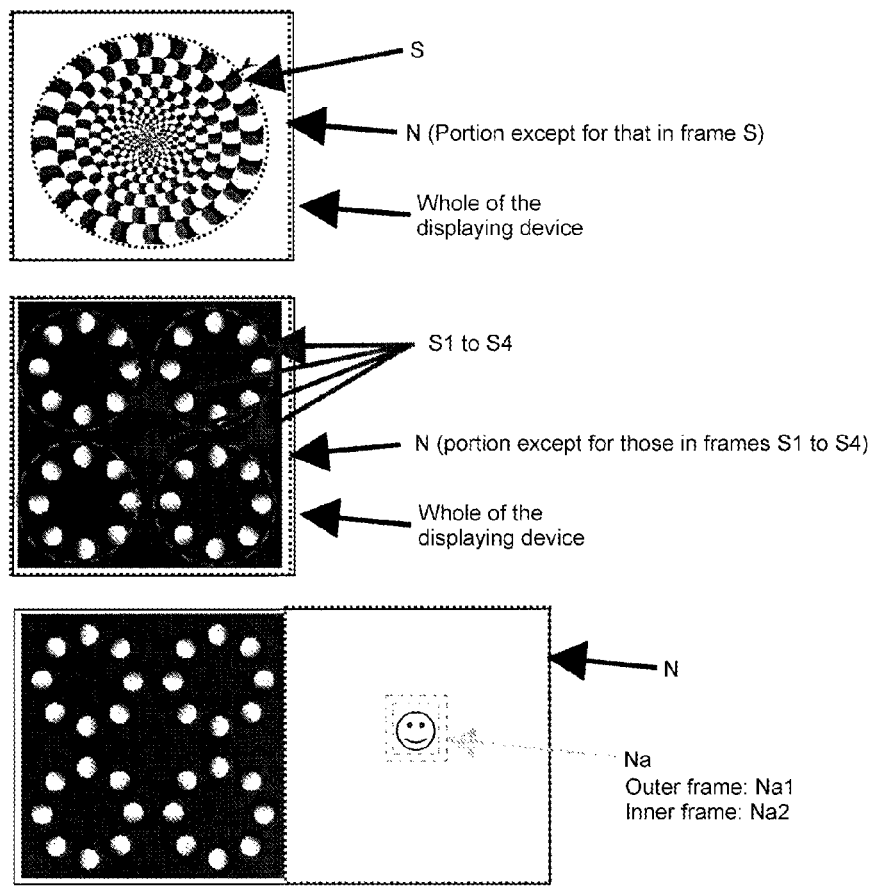
FIG. 22 is a figure showing one example explaining specific non-illusionary area N.

Next, the whole area in the image displayed on Display Unit B outside illusionary area S is defined as "non-illusionary area N" (see FIG. 22). When illusionary area S is displayed only in a portion of the displayed image, all of the area of the displayed image other than illusionary area S is non-illusionary area N. When illusionary area S completely occupies all of the area of the displayed image, non-illusionary area N is the area outside the displayed image. When illusionary area S is not displayed, all of the area of the image displayed on Display Unit B is non-illusionary area N.

An image (pattern) causing no optic illusion may be displayed in non-illusionary area N outside the outer edge of illusionary area S (see right half of the lowermost image in FIG. 22).

The area of this image (pattern) is included in non-illusionary area N. When a plurality of non-illusionary area N are present, these non-illusionary areas are numbered Na, Nb . . . for convenience and, when a plurality of non-illusionary areas each having a shape with geometrical similarity and increase in size is set for each image, the non-illusionary areas overlapping to each other, with respect to each groups of the non-illusionary areas, these non-illusionary areas are numbered Na1, Na2 . . . from the non-illusionary area with the outermost outer edge for convenience, in substantially the same manner as in the definition of illusionary area S.

It is not necessary to set the outer edge of each non-illusionary area exactly along the outer edge of each image (pattern) like trimming. The outer edge may be set in substantially the same manner as illusionary area S, i.e., non-illusionary area N arbitrarily set so as to have an outer edge with a simple shape (such as a rectangle, circle or the like), as shown for the above-mentioned non-illusionary area Na.

In the setting of non-illusionary area N, attention should be paid to the fact that clear definition as to what portion of the area outside the screen of Display Unit B should be calculated as non-illusionary area N (or whether or not the area outside the screen of Display Unit B should be excluded from calculation (as error or the like)) is preferred, depending on the specification of the Eye-gaze Position Detecting Unit employed.

Any of these definitions may be selected, depending on the specification of the Eye-gaze Position Detecting Unit employed. It is preferred to pay careful attention to avoid adverse effect to comparison with the previously obtained information of the detected results derived from the difference in manner of calculation related to non-illusionary area N.

Each of illusionary area S and non-illusionary area N specified as mentioned above, with the number, size and the like of each area appropriately set by optional adjustment depending on the object of analysis intended by the Inspector. The information of position related to illusionary area S and non-illusionary area N is managed in Body Unit as information of position in the image displayed on Display Unit B.

Needless to say, when the image displayed on Display Unit B is changed over time, the information of position related to illusionary area S and non-illusionary area N is consistent with the image displayed to the subject and when the image is stereoscopically displayed, three-dimensional information is added.

The following setting is an example in which illusionary area S and non-illusionary area N can be commonly and easily set irrespective of the shapes and sizes of the images.

The whole image displayed on Display Unit B is evenly divided into a plurality of square areas each having the same size. Each square area may be set as belonging to illusionary area S or non-illusionary area N based on the criterion that the whole (or half or more) of the square area overlaps the image.

In this case, fine division into the square areas each having the size as small as possible is preferred. However, depending on the size, shape, position or the like of the image to be displayed, coarse division in which the whole image is divided evenly into square areas each having relatively large size or uneven division in which the whole image is divided unevenly into square areas with different sizes appropriately adjusted (to relatively large size, with respect to some of the square areas) so that the square areas appropriately fit the shape of the outer edge of the image may be employed. Each square area may be set as belonging to illusionary area S or non-illusionary area N.

In an extreme case, the whole image including an illusionary image is divided into square areas each having relatively large size (but smaller than the size of the illusionary image), with each square area at least partially overlapping the illusionary image set as belonging to illusionary area S and each of other square areas (not overlapping the illusionary image) set as belonging to non-illusionary area N.

(a-3) Addition of the Areal Information to the Image Information in the Information of Image to be Displayed After the setting of the areas in the image, the above-mentioned areal information related to "illusionary area S" or "non-illusionary area N" is added to the image information (with respect to all images to be displayed on Display Unit B) in Body Unit.

In this addition, the areal information of each image may be automatically determined in Body Unit based on color data of the screen, or made to be manually set or adjusted by the inspector or the like.

The information may be retained in the displayed image itself with colorless line(s) invisible to the subject. Alternatively, the information may be retained separately from the displayed image in another image or in the form of positional information and made consistent with the displayed image at the time of analysis.

This addition may be conducted before or after the display of the image to the subject, as long as the addition is completed before the receipt and analysis of eye gaze position information as the stored information by Body Unit.

A specific example of the position-in-area information related to illusionary area S and non-illusionary area N is given below.

Figure 23:
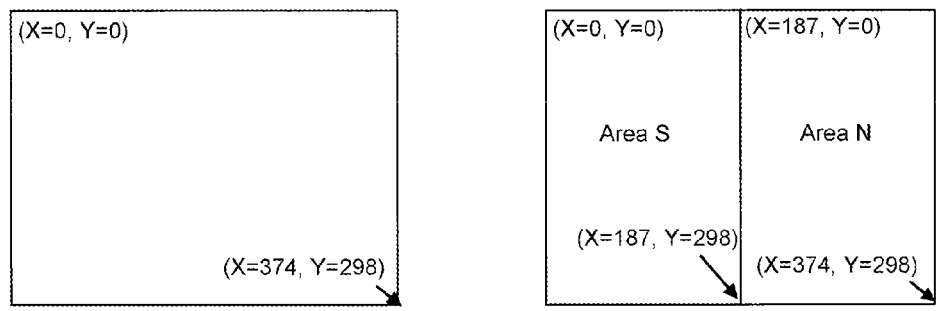
FIG. 23 is a figure showing one example explaining position-in-area information with areas S and N defined.

The left figure of the two figures in FIG. 23 shows an example of a matter displayed in a liquid crystal display as Display Unit B in the above-mentioned item (3).

Hereinbelow, the position in the display (number of pixels of the horizontal side: number of pixels of the vertical side=1280:1024) is specified using a coordinate system based on the positions of pixels in the display. A rectangular area with the length of the horizontal side of 374 and the length of the vertical side of 298 is provided in the display. The upper left corner of the rectangular area is defined as the origin of the coordinate system. The pixels constructing this rectangular area exactly correspond to a portion of pixels of the display. In accordance with this coordinate system, the position of the origin, the upper left corner of the rectangular area is specified as (X=0, Y=0), and the position of the lower right corner of the rectangular area is specified as (X=374, Y=298). The eye gaze positions and position-in-area information are also specified using this coordinate system and made consistent with the positions of pixels of the display.

If an illusionary image is displayed across the left half of this rectangular area (as shown in the right figure in FIG. 23), illusionary area S is set as a rectangular area surrounded by a rectangular outer edge with the position of the upper left corner of (X=0, Y=0) and the position of the lower right corner of (X=187, Y=298). On the other hand, non-illusionary area N is set as a rectangular area surrounded by a rectangular outer edge with the position of the upper left corner of (X=187, Y=0) and the position of the lower right corner of (X=374, Y=298).

Figures 24, 25:
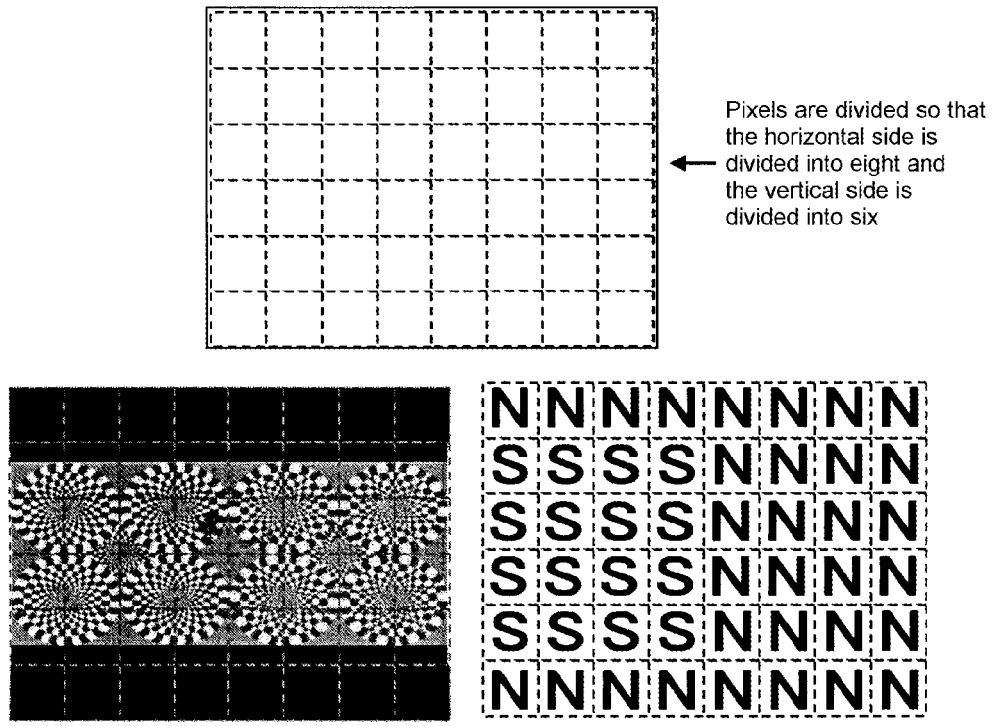
FIG. 24 is a figure showing another example explaining position-in-area information.
FIG. 25 is a figure showing one example explaining the data of eye-gaze position information.

In the above-mentioned example in which illusionary area S and non-illusionary area N are commonly and easily set for various images, setting of areas may be applied to the square areas produced by vertical and horizontal division of the pixels (as shown in FIG. 24). In FIG. 24, pixels are to 48 square areas by the division of the horizontal side into eight and division of the vertical side into six and, each square area overlapping the illusionary image is set as illusionary area S and each of other square areas not overlapping the illusionary image is set as non-illusionary area N.

Using this manner of setting of areas, each square area of any image displayed on Display Unit B can be made consistent with the positions of pixels of the display, based on the coordinate system of pixels. The position-in-area information retained in Body Unit enables easy identification, using the coordinate system of pixels of the display, as to what position the subject looks at, when the subject looks at the position, and in which the position is present, illusionary area S or non-illusionary area N.

(b) Eye-Gaze Position Information

The eye-gaze position information (which is input from Eye-gaze Position Detecting Unit by Body Unit) is information including the data of eye-gaze positions using the coordinate system which enables checking by Body Unit as to what position of Display Unit B the subject looks at.

Examples of the eye-gaze position information include information in which the eye-gaze positions of the subject are expressed as two-dimensional data (i.e., using an X-Y coordinate system).

It is preferred that time information (such as information of actual time determined by an atomic clock or the like) which clearly shows the time when the subject looks at a certain position of the information of image to be displayed is added to the detected eye-gaze position information, since such information ensures consistency of the stored information later.

Detailed explanation of the eye-gaze position information detected by the eye-gaze position detecting unit is made below. The eye-gaze position information may be originally detected as numeral data (such as two-dimensional data (X, Y) corresponding to relative position in a coordinate system applied to an image displayed on Display Unit B, and absolute positional data in a coordinate system not related to the position in an image displayed on Display Unit B and unique to the imaging camera portion, the positional data calculated from the eye-gaze position obtained from the image taken by the imaging camera portion of the eye-gaze position detecting unit) or detected from the plotted points combined with an image displayed on Display Unit B, the plotted points obtained as image data (i.e., not as numeral data) from the image taken by the imaging camera portion.

That is, there is no particular limitation with respect to the type of the eye-gaze position information (i.e., the eye-gaze position information is not limited to be in the form of numeral data or image data), as long as the position and time of the eye-gaze position information can be specified without inconsistency with the information of image to be displayed.

The eye-gaze position information is not limited to be in the form of two-dimensional data (X, Y) corresponding to a position in a coordinate system related to a planer image displayed on a screen, i.e., may be three-dimensional data (X, Y, Z) corresponding to a position in a coordinate system related to a stereoscopic image.

In such three-dimensional data, the eye-gaze position is a point in which the eye gaze position of each of both eyes overlaps in front of the eyes of the subject (in other words, "point of view"). In the present invention, this point can be regarded as substantially the same as the eye gaze position as two-dimensional data, i.e., the point of intersection of the screen of the displaying device by the eye gaze. In other words, detection of the eye gaze as information of not only planer position but also stereoscopic position (i.e., detection as point of view) is included in the definition of eye gaze in the present invention.

As one specific example, supplemental explanation of the eye-gaze position information for the unit for detecting points of regard produced by Shizuoka University (described in the above-mentioned PATENT LITERATURES 1 to 5 and item (2) above) is made below.

The eye-gaze position detecting unit in item (2) above is appropriately adjusted so that detection of the eye-gaze position of the subject is conducted 60 times per second, each of the eye-gaze positions being the position which is looked at by the subject specified as two-dimensional data (X, Y) corresponding to a position in a coordinate system applied to an image displayed on a display. The eye-gaze position information of the subject output comprises information of these eye-gaze positions detected.

For example, when an illusionary image is displayed only in the left half of the screen of a liquid crystal display (19 inch) as described above for 40 seconds and data acquisition rate is changed to 30 times per second, the eye-gaze position information is obtained as 1200 (30 times×40 seconds) data points in the form of two-dimensional data (X, Y) each corresponding to a certain position in a coordinate system applied to an image displayed on the display.

More specifically, as described later, the processing of the obtained data in Body Unit gives the data of eye-gaze position information as shown in FIG. 25.

(c) Stored Information

Stored information means information stored as the data to be analyzed which is related to eye-gaze positions, which information comprises information of image to be displayed (including the areal information) which is transmitted to Display Unit B and information of eye-gaze positions input from the eye-gaze position detecting unit, both stored in Body Unit for ensuring consistency of information related to positions.

Any supplemental information other than the above-mentioned position-in-area information and information of eye-gaze positions may be added to the stored information. Examples of such supplemental information include the title of the image file, history of display time, information of the specification of the unit used, personal information of the subject, history of previous diagnoses and the like.

Based on the stored information, Body Unit conducts a predetermined analysis of (the frequency of) the eve-gaze movement from the determined eye-gaze position information of the subject.

The predetermined analysis means calculation, from the information of eye-gaze positions and information of image to be displayed, as to what position (area) of the areal information in the information of image to be displayed the subject looks at and in what frequency the eve-gaze movement between some specific areas occurs, and presentation of the results of the calculation.

The above-mentioned matter is explained with reference to FIG. 25. The item "Position coordinate" shows the information of eye-gaze positions (positions of eye-gaze detection) which is consistent with the position stored in the form of two-dimensional data (X, Y) for a coordinate system applied to an image displayed on Display Unit B. The item "Number" shows the order of detections and the item "Acquisition time" shows the point of time of detection. These are supplemental information for the stored information. The item "Presence (area)" shows information of judgment of each square area (set for each image in FIG. 24) with the areal information (illusionary area S or non-illusionary area N). Each of the items "S→N" and "N→S" shows the presence or absence of the eye-gaze movement between illusionary area S and non-illusionary area N. These matters are described in a comma-separated text data in the order of detection.

The calculation may be conducted totally for all images displayed to the subject or separately for each of a specific unit of period of time of examination or for each image displayed.

If necessary, it is preferred to conduct calculation for obtaining the difference between the stored information obtained in the instant examination with the stored information as reference information previously obtained with respect to typically developing individuals and/or individuals with autism using the images which is the same as those used in the instant examination.

In this analysis, appropriate setting of specific square areas and areal information of the image is important. Such setting gives appropriate criterion for calculation of the frequency of eye-gaze movement of the subject, and enables evaluation of stored information of typically developing individuals and/or individuals with autism based on the contrast or difference in tendency of eye-gaze movement.

Supplemental explanation is made with reference to a specific example in which the eye-gaze position information is obtained as 1200 data points during the 40 seconds of examination from the image vertically and horizontally divided into 48 square areas (as in the above-mentioned FIG. 24), using the eye-gaze position detecting unit in the above-mentioned item (2).

Calculation of the eye-gaze position information is obtained as 1200 data points and position-in-area information for the information of image to be displayed in Body Unit may give, for example, the following information.

The number of eye-gaze positions found in each of illusionary area S and non-illusionary area N (hereinbelow, a position in an image is referred to as "plot")

(i) Total number of plots found in illusionary area S (998 of 1200)

(ii) Total number of plots found in non-illusionary area N (202 of 1200)

(iii) Number of first plots moved from illusionary area S to non-illusionary area N (2 in total)

(iv) Number of first plots moved from non-illusionary area N to from illusionary area S (2 in total)

As apparent from the above, the sum of number of plots of (i) and (ii) almost equals to the total number of plots (1200), and the numbers of (iii) and (iv) are almost the same because of tendency of reciprocation. For this reason, with respect to each of these combinations of calculations, only one calculation may be conducted. However, in view of verification of the detected information, conduction of both of these calculations is preferred.

In addition to the calculations above related to the accumulated total number or number of movement for each area, calculation of the longest time of presence in the same area, average number of presence in the same area and the like can be easily conducted.

Needless to say, it is not necessary to conduct the above-mentioned counting with respect to the number of plots. This counting can be achieved by, for example, counting the difference in time between neighboring two data points containing the same plot as the time of presence of the plot. Alternatively, the time period necessary for the eye-gaze detecting unit to obtain 1 plot may be counted as the time of presence of the plot (for example, with respect to the eye-gaze detecting unit detecting 30 plots per second, 1/30 sec per 1 plot). The unit for this counting can be arbitrarily determined.

As apparent from the above, calculation with respect to each area (more specifically, the average number of retention) enables understanding of degree of regard of the subject to a specific area. Such calculation is preferred, since it is possible that eye gaze moves once from area 1 to area 2 and returns to and is concentrated to area 1.

When a plurality of illusionary areas S and/or non-illusionary areas N are present in one image or a plurality of images are used, calculation to obtain total number for all of illusionary areas S (or non-illusionary areas N) in combination is preferred. However, optional calculation with respect to each of these areas (i.e., for example, separately with respect to illusionary area S1, illusionary area S2 and the like) may be conducted.

Alternatively, the distance of eye gaze movement between two plots may be converted into the direction and magnitude of a vector to calculate, as a portion of information, the frequency and/or velocity of eye gaze movement.

As apparent from the above, setting of these areas (in other words, areal information) enables easy calculation of the eye-gaze position information of the subject mainly regarding illusionary area S as the base of movement, which calculation may contribute effective analysis and/or comparison, such as tendency of retention of eye gaze within illusionary area S and tendency of eye gaze movement into illusionary area S from an area outside illusionary area S (or from illusionary area S into an area outside illusionary area S).

Further, the stored information in Body Unit enables detection of change in tendency of eye gaze movement relative to previously detected tendency of the same subject (using the same information of image) or difference in tendency of eye gaze movement between different subjects (using the same information of image).

Comparison of the stored information with previously obtained stored information of an individual who has already definitely diagnosed as a typically developing individual/individual with autism (using the same information of image) also becomes easy.

Such stored information may provide improved convenience in that:
(i) when a subject with previous stored information is definitely diagnosed as a typically developing individual/individual with autism later, the previous stored information may be stored as supplemental information to reinforce the effectiveness of the stored information as reference information, and
(ii) an examination itself only for obtaining stored information can be conducted, even in an area with a small number of experts (specialists) or in a case with no expert (specialist) present (such as a group examination in a school or local health center), and the definite diagnosis can be made by an expert (specialist), later or immediately for early detection, based on the evaluation result of the stored information, even in a distant place using a communicating means, or recommendation by a doctor of another medical field or the like to obtain definite diagnosis by an expert (specialist) based on the evaluation result of the stored information (accompanied by notice of the stored information to the expert (specialist)) becomes available.

In such stored information, for further investigation which the inspector desires, it is preferred to add supplemental information for various manner of classification of the reference (target for comparison), such as classification by age, gender or external characteristics.

In the present invention it is preferred to set a threshold value for the frequency of mutual eye-gaze movement between an area of the plane of an illusion-causing image in which the illusionary image is displayed and an area of the plane of an illusion-causing image in which the illusionary image is not displayed, based on a database having stored therein previously obtained information of eye-gaze positions of subjects and definite diagnosis of each of the subjects as to whether or not the subject is an individual with autism.

(d) Information of the Detected Results

Information of the detected results is information of the content of analysis of the stored information by Body Unit to be displayed to the inspector, printed or transferred in a format which the inspector desires. The display, print or transfer of this information includes output of information of the (still or moving) image not only by display on Display Unit A but also output by print by a printing device, output to an external storage media, playback device or another displaying device, and the like.

Information of the detected results may not be expressed by values (as the above-mentioned values (i) to (xi)). This information may be expressed as a figure in which the number or time of concentration of eye gaze is converted to a various kind of distribution map, such as a concentration distribution map (as the above-mentioned (i) and (ii)). This information may not be expressed the content of analysis of the stored information. For example, this information may be expressed as a moving image recorded as information of image to be displayed and information of eye-gaze positions or a still image with eye gaze movement reproduced in various manners, such as superimposed trajectory of eye gaze movement with changed color.

Figure 26:
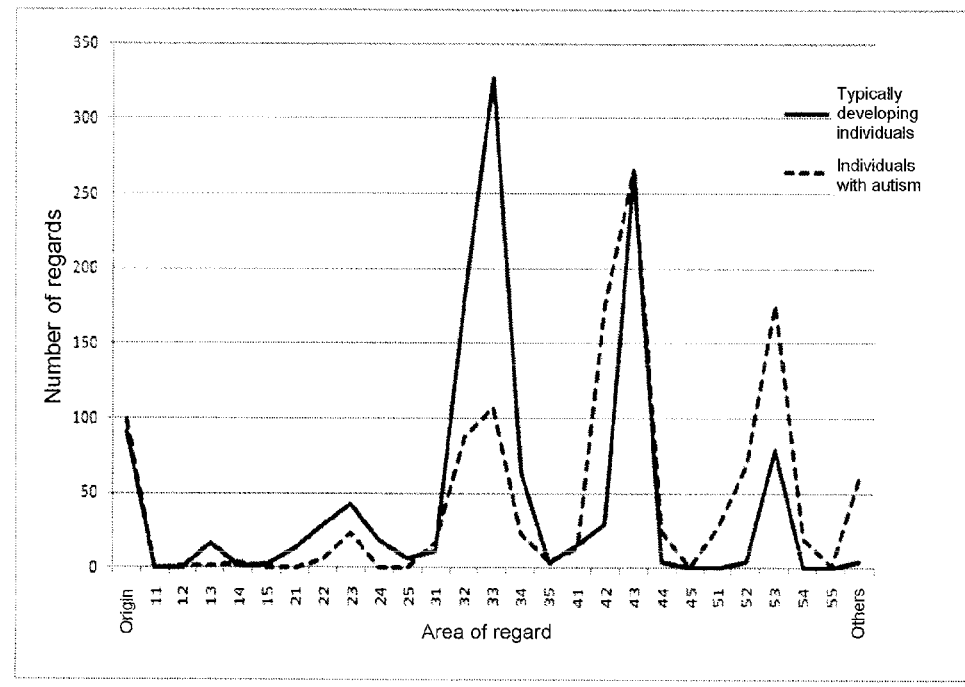
FIG. 26 is a figure showing one specific example of information of the results of detection.
Figure 26:
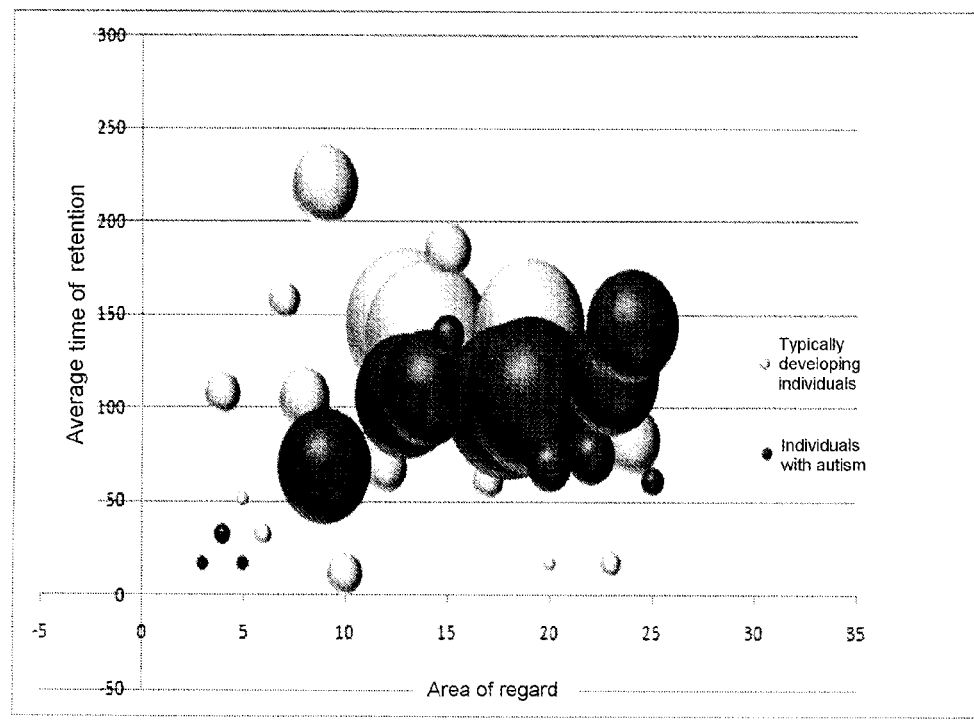

A specific example of the information of the detected results is given below. The results of calculation may be displayed to the inspector in the form of various kinds of figures or graphs, such as a line graph, bubble chart, scatter diagram, bar graph or circle graph, as done in A and B of FIG. 26. In FIG. 26A, the data (obtained separately with respect to typically developing children and children with autism) of the accumulated total time (number) of detection of eye-gaze positions in each area formed by division of the screen vertically into five and horizontally into five is presented in the form of a line graph. In FIG. 26B, the same data is presented in the form of a bubble chart (with the vertical axis as average time of presence) for comparison. By each of these presentations, the inspector is visually provided with the contrast or difference in tendency of eye-gaze movement between typically developing individuals and individuals with autism which may be easily compared and investigated.

It is preferred that the data presented for comparison is appropriately selected based on an individual from which the data is obtained or the like, if necessary. Further, the data for the presentation may be an average (standard) value calculated from some appropriately selected data. These data may be appropriately combined.

The above-mentioned manner of presentation of the content of analysis of the stored information is suitable as the eye-gaze position information to show potential symptom(s) of autism to the inspector.

II. Flow of Eye-Gaze Detection

Specific flow of eye-gaze detection for the system for assisting diagnosis of autism is explained below. This system comprises the following steps.

Step I: Preparation for the detection
Step II: Start of the detection
Step III: Processing of the data of eye-gaze positions
Step IV: Presentation of the results of evaluation of eye-gaze positions 1. Step I: Preparation for the Detection First, as preparation for the detection of Step I, a subject is made seated at an appropriate position, for example, at the position right in front of and about 80 cm away from the display. When the subject is an infant, the subject may be seated on the lap of his/her mother or the like. The screen of the display is set at an appropriate height and position so that the screen is fully come in sight of the subject.

A certain eye-gaze detection technique (for example, the technique of one of the above-mentioned PATENT LITERATURES 1 to 8) is applied to the above-mentioned eye-gaze detecting unit. This unit is set at a position sufficient for detecting eye-gaze positions of the subject. Optionally at this stage (especially when check of this unit is necessary to confirm that the eye-gaze position determined by this unit is in conformity with the actual eye-gaze position the subject), tuning of this unit (adjustment of position for each subject, check of accuracy of detection error, and the like) is conducted. If the subject has previously been examined using the same unit, it is preferred that the tuning is conducted using the information obtained in this examination.

As the images to be shown displayed in the screen of the above-mentioned display, one or more of the images of Table 1 above to be used for eye-gaze detection (edited into the arrangements of (i) to (iii) of Table 2 above) is/are prepared in advance.

Each of the prepared images comprises "illusionary area S" and/or "non-illusionary area N", and the areal information related to these areas corresponds the change of images over time.

In the present invention, it is preferred that in the screen of the display, the following images (a) and (b):
(a) an illusionary image causing optic illusion that the image is seemingly moving when the eyes are pulled slightly away, and
(b) a non-illusionary image causing no optic illusion are arranged in parallel (as those of (ii) and (iii) in Table 2 (corresponding to FIGS. 18 and 19)), in order to avoid intended leading of moving of the eye gaze of the subject or let the subject voluntarily look at images displayed.

Only one image may be displayed. However, it is preferred to display a plurality of images in series, in view of extensive collection of information (personality, interest and the like) of each subject. It is preferred to that among these images, there is an image in which an image causing optic illusion is shown in the left half and another image causing no optic illusion is shown in the right half (like (iii) in Table 2 (corresponding to FIG. 19)).

Step II: Start of the Detection

When a personal computer (PC: the device for assisting diagnosis of autism) receives a signal from a doctor (inspector) to start the eye-gaze detection, the PC displays particular images used for the detection. The time of display is from several seconds to several tens of seconds and appropriately adjusted as the doctor requests.

The subject thus looks at the prepared image(s).

The eye-gaze position information of the subject corresponding to the prepared particular illusionary image is chronologically transmitted from the eye-gaze detecting unit to the PC. At this time, time stamp is added to the eye-gaze position information.

The eye-gaze position information unsuitable for evaluation (because of the time in which the subject does not look at the screen or blink of the subject) may be added marking information for exclusion or subjected to deletion treatment at this or later stage so that the information is regarded as unnecessary information. When the subject is an infant, it is possible that the time in which the subject does not look at the screen is too long. In this case, the manner of the eye-gaze detection may be appropriately arranged so that the eye-gaze detection is re-started or resumed after suspension. The interest of the subject may be attracted by the stimulation with, for example, some sound (music, voice of parents or the like) from the direction of the display.

The eye-gaze detection is completed when the display of all of the prepared images at the request of the doctor is completed.

Step III: Processing of the Data of Eye-Gaze Positions

Figure 4:
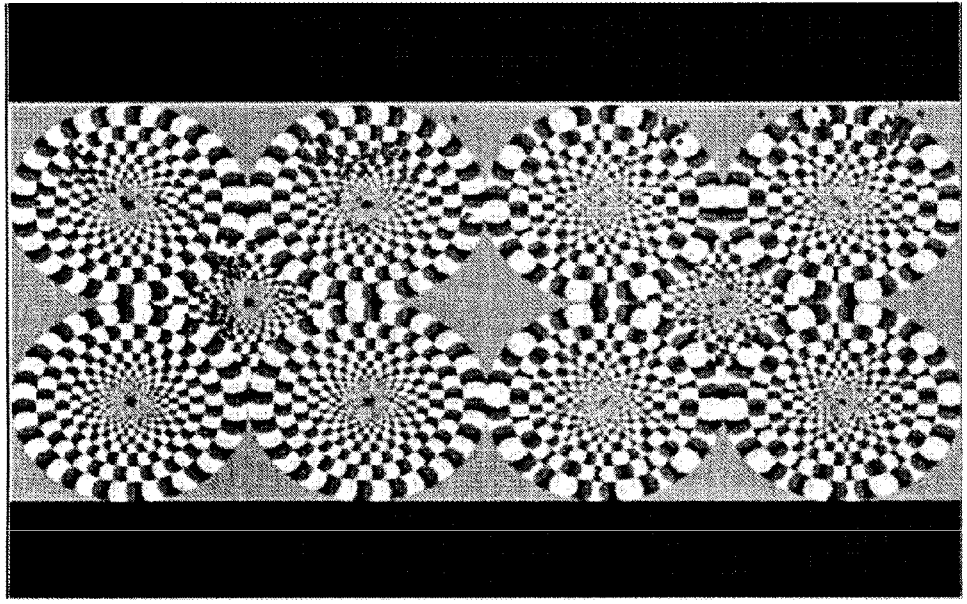
FIG. 4 is a figure showing one example of indication of eye-gaze position information for the method and system of the present invention for assisting diagnosis of autism.
Figure 4:
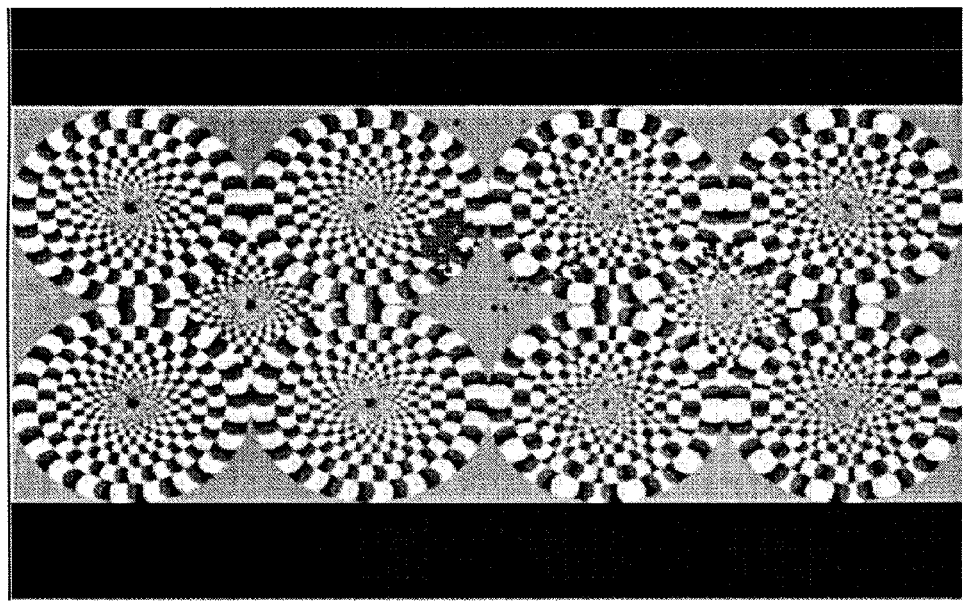

The collected eye-gaze position information is scored by the PC as shown in FIG. 4, based on the areal information. The areal information is information with respect to judgment for each eye-gaze position of each time stamp as to in which area of the displayed image the eye-gaze position is detected, the above-mentioned "illusionary area S" or "non-illusionary area N" (both of which the displayed image comprises).

The manner of this scoring may be arbitrarily selected. For example, each value itself obtained as the eye-gaze position information may be directly scored, or appropriate information derived from the eye-gaze position information originally obtained as images (comprising plots each containing eye-gaze positions) may be scored.

In this case, the scoring related to the judgment of "illusionary area S" or "non-illusionary area N" (contained in an image displayed on a screen of a display) is conducted based on the following information.

(a) the position (as two-dimensional data (X, Y) corresponding to a position in a coordinate system applied to the image displayed on the screen) and period of time of the presence of the element inducing eye-gaze movement on the screen of the display (b) the number of movements of the eye-gaze positions from "illusionary area S" to "non-illusionary area N", or the longest time for each of these areas in which the eye-gaze position is continuously present in each area In this scoring, the frequency of mutual eye-gaze movement between "illusionary area S" and "non-illusionary area N" may be compared with the eye-gaze position information of typically developing individuals or individuals with autism, based on a database having stored therein previously obtained information of eye-gaze positions of subjects and definite diagnosis of each of the subjects as to whether or not the subject is an individual with autism.

The processing of the data is completed when the scoring of all of the images the displayed in the examination is completed.

When an image with the left half indicating an illusionary image causing optic illusion and the right half indicating an image causing no optic illusion (like (iii) in Table 2 (corresponding to FIG. 19)) is used, the tendency of eye-gaze movement of typically developing subjects is characterized by remarkable horizontal movement of eye gaze because of optic illusion in the left half recognized by the subjects, whereas the tendency of eye-gaze movement of subjects with autism is characterized by less horizontal movement of eye gaze because of regard of the subjects concentrated to a certain point in the image.

Step IV: Presentation of the Results of Evaluation of Eye-Gaze Positions

As a result of the above-mentioned process, the results of evaluation of eye-gaze positions is presented in the PC, like the manner as in A and B in FIG. 26.

From the results of evaluation of eye-gaze positions presented in the PC, a doctor can detect, based on the difference in tendency of eye-gaze movement between typically developing individuals and individuals with autism, the tendency of eye-gaze movement of an individual with autism. As a result, early definite diagnosis of autism of a patient becomes possible.

III. Device for Assisting Eye-Gaze Detection

The device of the present invention for assisting eye-gaze detection is a device for assisting diagnosis of autism using an illusionary image, which comprises:

(i) an eye-gaze detecting portion which detects eye-gaze position information of a subject looking at a plane of an illusion-causing image displayed at the position in front of the subject along the direction of the eye gaze of the subject using an eye-gaze detecting means, (ii) an eye-gaze information recording portion which records the eye-gaze position information detected by the eye-gaze detecting portion (i), (iii) an eye-gaze information displaying portion which displays the eye-gaze position information of the subject recorded by the eye-gaze information recording portion (ii), (iv) an eye-gaze information evaluating portion which conducts evaluation of the eye-gaze position information of the subject displayed by the eye-gaze information displaying portion (iii) using a predetermined algorithm for assisting diagnosis of autism with respect to analogy to eye-gaze information of typically developing individuals or individuals with autism, (v) an evaluation result outputting portion which outputs the evaluation results obtained by the eye-gaze information evaluating portion (iv), and (vi) an evaluation result recording portion which records the evaluation results output by the evaluation result outputting portion (v) or obtained by the eye-gaze information evaluating portion (iv).

The device of the present invention for assisting eye-gaze detection is formed by embodying the above-mentioned system for assisting diagnosis of autism (which is explained above in detail) as an actual device.

EXAMPLES

Hereinbelow, the present invention will be described in more detail with reference to the following Examples, which should not be construed as limiting the scope of the present invention.

Example 1

In accordance with the above-mentioned flow of eve-gaze detection in the present specification, each of one typically developing individual (typically developing child, 7-years old) and one individual with autism (child with autism, 7-years old) was subjected to the eye-gaze detection examination using the system for assisting diagnosis of autism with steps I to IV.

Figure 3:
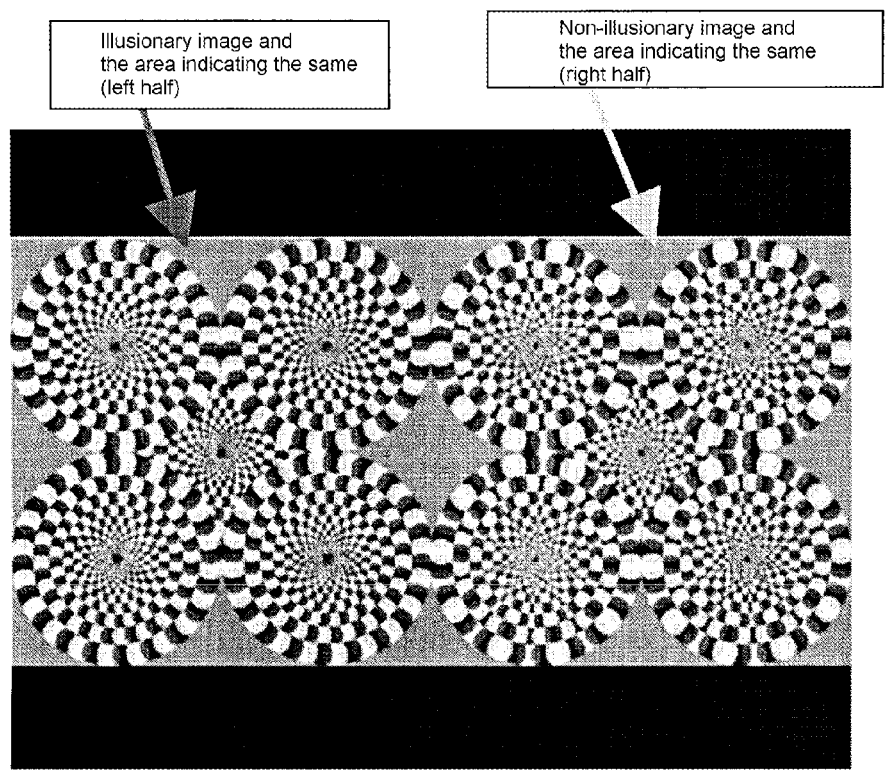
FIG. 3 is a figure showing another example of the plane of an illusion-causing image.

More specifically, the plane of an illusion-causing image shown in FIG. 3 (with one set of 4 rings positioned in the left half of the image which causes optic illusion and another set of 4 rings positioned in the right half of the image which causes no optic illusion) was shown on a display of a personal computer in accordance with a signal from the doctor to start the eye-gaze detection. This plane was displayed to the above-mentioned two subjects (one typically developing individual and one individual with autism) for six seconds. As a result, the results of evaluation of the eye-gaze positions (containing the data of scores counted for each eye-gaze position) was displayed as shown in FIG. 4.

The results of calculation from the obtained information are given in Table 3 below.

|  | Image of FIG. 3 (displayed on Display Unit B for 6 seconds) | | |
|---|---|---|---|
|  | Typically developing child | Child with autism | Standard values as reference |
| Total number of plots detected by the eye-gaze position detecting unit |  | 180 |  |
| (a) Number of plots in which an eye gaze is detected in area S | 115 | 129 | 102 |
| (b) Number of plots in which an eye gaze is detected in area N | 54 | 41 | 58 |
| (c) Average time of presence of eye-gaze position in area S (sec) | 0.9 | 1.4 | 0.7 |
| (d) Average time of presence of eye-gaze position in area N (sec) | 0.4 | 1.4 | 0.3 |
| (e) Longest time of presence of eye-gaze position in area S (sec) | 1.8 | 4.0 | 1.6 |
| (f) Longest time of presence of eye-gaze position in area N (sec) | 1.0 | 1.4 | 0.8 |
| (g) Number of movements of eye gaze between areas S and N (times) | 7 | 2 | 9 |

| | Image of FIG. 3 (displayed on Display Unit B for 6 seconds) | | |
|---|---|---|---|
| | Typically developing child | Child with autism | Standard values as reference |
| Number of point excluded for accuracy of information (caused by plot error, measurement error etc.) | Others 11 | Others 10 | Others 18 |

The above results of evaluation clearly show that the results of the typically developing individual (child) are similar to the standard values (a) to (g) as reference obtained from ten typically developing children, whereas the results of the individual (child) with autism show significant difference from the standard values (a) to (g) as reference. These results were sufficient for detection of the tendency of eye-gaze movement of subjects with autism by an expert (specialist) and useful for early definite diagnosis of autism.

Although infants were subjected to examination in this Example, it was separately confirmed that substantially the same results of calculation were the obtained if the subjects were adults.

INDUSTRIAL APPLICABILITY

The method and system of the present invention for assisting diagnosis of autism is advantageous in that assistance of early detection and early definite diagnosis of autism (even in an infant before the age that the identification by a specialist as an individual with autism can be applied to) based on objective evaluation becomes possible.

The invention claimed is:

1. A method for assisting diagnosis of autism of a subject using an eye-gaze detecting unit, said unit having at least an imaging camera portion,
said method comprising:
displaying on a first display, at a position in front of said subject along a direction of an eye gaze of said subject, (a) a particular illusionary image which is an image causing optic illusion that said image is seemingly moving when the eyes are pulled slightly away and (b) a non-illusionary image causing no optic illusion, the particular illusionary image and the non-illusionary image being arranged in parallel in a plane of an illusion-causing image, in order to avoid intended leading of moving of the eye gaze of said subject or let said subject voluntarily look at images displayed,
detecting, using the imaging camera portion, eye-gaze position information of said subject looking at said plane,
calculating an evaluation value of eye-gaze positions of said subject based on the detected eye-gaze position information, and
displaying the calculated evaluation value on a second display with comparison to an evaluation value of eye-gaze positions of typically developing individuals,
wherein the eye-gaze positions given in said eye-gaze position information are detected in the following areas (i) and (ii) of said plane:
(i) an area in which said illusionary image is displayed, and
(ii) an area other than said area (i), and
wherein the step of calculating the evaluation value comprises calculating, as the evaluation value, a value representing one of the following (a) to (c):
(a) an accumulated total time or average time for each of said areas (i) and (ii) in which the eye-gaze positions are present in each area,
(b) a number of movements of the eye-gaze positions from said area (i) to said area (ii), or
(c) a longest time for each of said areas (i) and (ii) in which the eye-gaze position is continuously preset in each area.

2. The method according to claim 1, wherein said non-illusionary image (b) is an image which is similar to said particular illusionary image (a) in appearance and color but causes no optic illusion that said image is seemingly moving even when the eyes are pulled slightly away.

3. The method according to claim 1, wherein the step of displaying the calculated evaluation value on the second display comprises displaying the calculated evaluation value in a form of graph or chart, together with the evaluation value of the eye-gaze positions of the typically developing individuals.

4. A system for assisting diagnosis of autism, which comprises:
an eye-gaze detecting unit configured to detect, using an imaging camera portion, eye-gaze position information of a subject looking at a plane of an illusion-causing image displayed at a position in front of said subject along a direction of an eye gaze of said subject;
a first display for displaying said plane; and
a second display;
a non-transitory memory; and
a processor coupled to the memory and configured to:
display on the first display (a) a particular illusionary image which is an image causing optic illusion that said image is seemingly moving when the eyes are pulled slightly away and (b) a non-illusionary image causing no optic illusion, the particular illusionary image and the non-illusionary image being arranged in parallel in the plane of the illusion-causing image, in order to avoid intended leading of moving of the eye gaze of said subject or let said subject voluntarily look at images displayed,
receive the eye-gaze position information, which is detected by the eye-gaze detecting unit, of said subject when said plane is displayed on the first display,
calculate an evaluation value of eye-gaze positions of said subject based on the received eye-gaze position information, the evaluation value representing one of the following (a) to (c):
(a) an accumulated total time or average time for each of said areas (i) and (ii) in which the eye-gaze positions are present in each area,
(b) a number of movements of the eye-gaze positions from said area (i) to said area (ii), or
(c) a longest time for each of said area (i) and (ii) in which the eye-gaze position is continuously present in each area, and
display the calculated evaluation value on the second display, with comparison to an evaluation value of eye-gaze positions of typically developing individuals,
wherein the eye-gaze positions given in said eye-gaze position information are detected in the following areas (i) and (ii) of said plane:

(i) an area in which said illusionary image is displayed, and (ii) an area other than said area (i).

5. The system according to claim 4, wherein said non-illusionary image (b) is an image which is similar to said particular illusionary image (a) in appearance and color but causes no optic illusion that said image is seemingly moving even when the eyes are pulled slightly away.

6. The system according to claim 4, wherein the process of displaying the calculated evaluation value on the second display comprises a process of displaying the calculated evaluation value in a form of graph or chart, together with the evaluation value of the eye-gaze positions of the typically developing individuals.

* * * * *